(12) United States Patent
Adam

(10) Patent No.: US 9,868,683 B2
(45) Date of Patent: Jan. 16, 2018

(54) MULTI-FUNCTIONAL PHENOLIC RESINS

(71) Applicant: EMPIRE TECHNOLOGY DEVELOPMENT LLC, Wilmington, DE (US)

(72) Inventor: Georgius Abidal Adam, Edensor Park (AU)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/898,420

(22) PCT Filed: Jun. 13, 2013

(86) PCT No.: PCT/US2013/045579
§ 371 (c)(1),
(2) Date: Dec. 14, 2015

(87) PCT Pub. No.: WO2014/200486
PCT Pub. Date: Dec. 18, 2014

(65) Prior Publication Data
US 2016/0137570 A1    May 19, 2016

(51) Int. Cl.
C07D 301/27    (2006.01)
C07C 39/15    (2006.01)
(Continued)

(52) U.S. Cl.
CPC ............. *C07C 39/15* (2013.01); *C07C 37/20* (2013.01); *C07C 41/01* (2013.01); *C07C 43/1783* (2013.01); *C07C 67/00* (2013.01); *C07C 69/54* (2013.01); *C07C 213/02* (2013.01); *C07C 215/50* (2013.01); *C07C 231/02* (2013.01); *C07C 233/20* (2013.01); *C07C 263/10* (2013.01); *C07C 265/08* (2013.01); *C07D 301/28* (2013.01); *C07D 303/30* (2013.01); *C07D 303/36* (2013.01); *C08G 8/08* (2013.01); *C08G 8/28* (2013.01); *C08L 61/14* (2013.01)

(58) Field of Classification Search
CPC .. C07D 301/28; C07D 303/30; C07D 303/36; C07C 39/15; C08G 8/08; C08G 8/28; C08L 61/14
USPC ......................................................... 549/517
See application file for complete search history.

(56) References Cited

U.S. PATENT DOCUMENTS

| 773,510 A | 10/1904 | Lindsay et al. |
| 2,091,965 A | 9/1937 | Cherry |

(Continued)

FOREIGN PATENT DOCUMENTS

| CN | 88100768 A | 9/1988 |
| CN | 1047311 A | 11/1990 |

(Continued)

OTHER PUBLICATIONS

International Search Report and Written Opinion for International application No. PCT/US2013/045579, dated Dec. 2, 2013.
(Continued)

*Primary Examiner* — T. Victor Oh
(74) *Attorney, Agent, or Firm* — Pepper Hamilton LLP

(57) ABSTRACT

Disclosed herein are compositions and methods of making phenolic compounds and phenolic resins. The resins include multifunctional epoxies, amino glycidyl derivatives, alkanoate derivatives, alkyl ether derivatives, and multi-functional amines prepared from hydroxymethyl derivatives of novolac resin.

5 Claims, 7 Drawing Sheets

(51) Int. Cl.
*C08G 8/08* (2006.01)
*C08G 8/28* (2006.01)
*C08L 61/14* (2006.01)
*C07C 37/20* (2006.01)
*C07C 41/01* (2006.01)
*C07C 43/178* (2006.01)
*C07C 67/00* (2006.01)
*C07C 69/54* (2006.01)
*C07C 213/02* (2006.01)
*C07C 215/50* (2006.01)
*C07C 231/02* (2006.01)
*C07C 233/20* (2006.01)
*C07C 263/10* (2006.01)
*C07C 265/08* (2006.01)
*C07D 301/28* (2006.01)
*C07D 303/30* (2006.01)
*C07D 303/36* (2006.01)

(56) References Cited

U.S. PATENT DOCUMENTS

| | | | |
|---|---|---|---|
| 2,220,834 | A | 11/1940 | Bruson et al. |
| 2,541,142 | A | 2/1951 | Zief et al. |
| 2,980,676 | A | 4/1961 | Zuppinger et al. |
| 3,425,964 | A | 2/1969 | Stanley et al. |
| 3,726,835 | A | 4/1973 | Bertozzi |
| 3,741,799 | A | 6/1973 | Kulhanek et al. |
| 3,957,524 | A | 5/1976 | Doughty et al. |
| 4,003,873 | A | 1/1977 | Smith |
| 4,038,455 | A | 7/1977 | Wampetich |
| 4,256,844 | A | 3/1981 | Martin et al. |
| 4,301,083 | A | 11/1981 | Yoshimura et al. |
| 4,369,290 | A | 1/1983 | Evans et al. |
| 4,374,126 | A | 2/1983 | Cardarelli et al. |
| 4,623,701 | A | 11/1986 | Massingill |
| 4,661,568 | A | 4/1987 | Koenig et al. |
| 4,853,145 | A | 8/1989 | Schmid et al. |
| 4,883,826 | A | 11/1989 | Marugg et al. |
| 4,900,873 | A | 2/1990 | Kakemoto et al. |
| 5,028,458 | A | 7/1991 | Mineck |
| 5,354,798 | A | 10/1994 | Tsukahara et al. |
| 5,447,789 | A | 9/1995 | Griffin |
| 5,908,902 | A | 6/1999 | Pfeil et al. |
| 5,939,515 | A | 8/1999 | Guenther et al. |
| 5,965,671 | A | 10/1999 | Ma et al. |
| 6,004,892 | A | 12/1999 | Guenther et al. |
| 6,083,658 | A | 7/2000 | Kunita et al. |
| 6,297,178 | B1 | 10/2001 | Berbner et al. |
| 6,822,030 | B2 | 11/2004 | Olson et al. |
| 6,884,557 | B2 | 4/2005 | Kasai et al. |
| 6,906,130 | B2 | 6/2005 | Tutin et al. |
| 7,008,994 | B1 | 3/2006 | Waki |
| 7,045,471 | B2 | 5/2006 | Kobayashi |
| 7,989,128 | B2 | 8/2011 | Levy et al. |
| 8,084,567 | B2 | 12/2011 | Ogura et al. |
| 2004/0225048 | A1 | 11/2004 | Miura et al. |
| 2004/0247882 | A1 | 12/2004 | Kouchi et al. |
| 2004/0258845 | A1 | 12/2004 | Kasahara |
| 2007/0134283 | A1 | 6/2007 | Wang et al. |
| 2008/0075999 | A1 | 3/2008 | Izuhara et al. |
| 2009/0304919 | A1 | 12/2009 | Wagner et al. |
| 2010/0164368 | A1 | 7/2010 | Kong et al. |
| 2010/0215922 | A1 | 8/2010 | Rajaraman et al. |
| 2010/0285309 | A1 | 11/2010 | Barriau et al. |
| 2010/0294429 | A1 | 11/2010 | Hoevel |
| 2011/0071056 | A1 | 3/2011 | Saini et al. |
| 2012/0164288 | A1 | 6/2012 | Miller |
| 2013/0190424 | A1 | 7/2013 | Takamatsu et al. |

FOREIGN PATENT DOCUMENTS

| | | |
|---|---|---|
| CN | 1207114 A | 2/1999 |
| CN | 1259424 A | 7/2000 |
| CN | 1422881 A | 6/2003 |
| CN | 1631500 A | 6/2005 |
| CN | 1931852 A1 | 3/2007 |
| CN | 101245160 A | 8/2008 |
| CN | 102731768 A | 10/2012 |
| DE | 237512 A1 | 7/1986 |
| EP | 279475 A2 | 8/1988 |
| EP | 0398749 A2 | 11/1990 |
| EP | 0439259 A1 | 7/1991 |
| EP | 1122268 A1 | 8/2001 |
| EP | 1352888 A1 | 10/2003 |
| EP | 2149572 A1 | 2/2010 |
| JP | S55164267 A | 12/1980 |
| JP | H05140138 A | 6/1993 |
| JP | 9304924 A | 11/1997 |
| JP | 2000147773 A | 5/2000 |
| JP | 200420933 A | 1/2004 |
| SU | 1447816 A1 | 12/1988 |
| WO | 9303063 A1 | 2/1993 |
| WO | 9509200 A1 | 4/1995 |
| WO | 0222332 A1 | 3/2002 |
| WO | 2005023744 A2 | 3/2005 |
| WO | 2010006350 A1 | 1/2010 |
| WO | 2011003446 A1 | 1/2011 |
| WO | 2012043245 A1 | 4/2012 |

OTHER PUBLICATIONS

Ding et al., Synthesis and Adhesive Performances of Phenol Hydroxymethyl Acrylate, Chemistry and Adhesion (Jul. 30, 2003), (4) pp. 159-164.

"Epoxy Resins," accessed at http://web.archive.org/web/20130124024338/http://info.smithersrapra.com/downloads/chapters/Thermoset%20Resins.pdf, accessed on Mar. 15, 2017, pp. 155-174.

"Huntsman to Further Expand Multifunctional Epoxy Resins Capacity and Capability," accessed at https://web.archive.org/web/20120122201140/http://www.huntsman.com/eng/News/News/Huntsman_to_Further_Expand_Multifunctional_Epoxy_Resins_Capacity_and_Capability/index.cfm?PageID=8583&News_ID=8060&style=72, dated Sep. 14, 2011, p. 1.

"Multi-Functional & Specialty Resins," accessed at http://web.archive.org/web/20120315052244/http://ww2.momentive.com/Products/Main.aspx?id=1058, accessed on Mar. 15, 2017, p. 1.

"Epoxy Resins," Aditya Birla Chemicals, accessed at http://web.archive.org/web/20121215060508/http://www.adityabirlachemicals.com/products/epoxy_resins/epoxy_resins_overview.html, accessed on Mar. 14, 2017, p. 1.

"Epoxy resins," Aditya Birla Chemicals, accessed at https://web.archive.org/web/20120422152558/http://www.adityabirlachemicals.com/products/epoxy_overview01.htm, accessed on Mar. 15, 2017, pp. 3.

"Melamine," accessed at http://web.archive.org/web/20130120085738/http://en.wikipedia.org/wiki/Melamine, last modified on Dec. 8, 2012, pp. 10.

"Multifunctional, High Tg Epoxy Low-Flow Prepreg," accessed at http://web.archive.org/web/20120524083626/http://www.arlon-med.com/51N.pdf, accessed on Mar. 15, 2017, pp. 4.

"Multifunctional, High Tg Epoxy Low-Flow Prepreg," accessed at http://streamlinecircuits.com/wpcontent/uploads/2015/08/51N.pdf, accessed on Mar. 15, 2017, pp. 4.

"Phenolic Novolac and Resol Resins" Plenco, accessed at http://web.archive.org/web/20130110230432/http://www.plenco.com/phenolic-novolac-resol-resins.htm, accessed on Mar. 15, 2017, pp. 7.

"World Epoxy Resin Market," Market Report, Acmite Market Intelligence, pp. 1-12 (Oct. 2010).

Atta, A.M., et al., "Synthesis of Bisphenol a Novolac Epoxy Resins for Coating Applications," Journal of Applied Polymer Science, vol. 107, Issue 1, pp. 347-354 (Sep. 19, 2007).

Auchmoody, L.R., et al., "Effect of Calcium Cyanamide, on Growth and Nutrition of Planted Yellow-Poplar Seedlings," USDA Forest Service Research Paper Ne-265, pp. 1-14 (1973).

(56) References Cited

OTHER PUBLICATIONS

Cech, J., "Characteristics of Bis F and Phenol Novolac Epoxy Resins," accessed at http://www.emeraldmaterials.com/cms/cvc/micms_doc_admin.display?p_customer=EPMCVC&p_name=%2FTECHNICAL%20SERVICE%20REPORTS-PRESENTATIONS%2FCHEMISTRY%20AND%20COMPOSITION%20OF%20EPN%20RESINS.PDF, accessed on Mar. 15, 2017, pp. 6.

Cech, J., et al., "The Effectiveness of Toughening Technologies on Multifunctional Epoxy Resin Systems," accessed at https://web.archive.org/web/20160519051151/http://www.hubronspeciality.com/wp-content/uploads/2013/09/CVC-TB-400-The-Effectiveness-of-Toughening-Technologies-on-Multifunctional-resin-systems.pdf, accessed on Mar. 15, 2017, pp. 15.

Cheng, J., et al., "Synthesis and characterization of novel multifunctional epoxy resin," Chinese Chemical Letters, vol. 18, Issue 4, pp. 469-472 (Apr. 2007).

Extended European Search Report for European Application No. 13886810.4 dated Nov. 8, 2016, pp. 9.

Fitzgerald, P.A., "Solution Behaviour of Polyethylene Oxide, Nonionic Gemini Surfactant," Ph.D Thesis, pp. 140 (Dec. 2002).

Hesse, W., et al., "Phenolic Resins," Encyclpedia, of Industrial Chemistry, vol. 26, pp. 583-600 (2012).

International Search Report and Written Opinion for International Application No. PCT/US2013/071204 dated May 14, 2014, pp. 11.

International Search Report and Written Opinion for International Application No. PCT/US2012/062708 dated Jan. 9, 2013, pp. 11.

International Search Report and Written Opinion for International Application No. PCT/US2013/072593 dated May 16, 2014, pp. 11.

International Search Report and Written Opinion for International Application No. PCT/US2013/072619 dated May 12, 2014, pp. 11.

Liu, Y., et al., "Curing Behavior and Thermal Properties of Multifunctional Epoxy Resin with Methylhexahydrophthalic Anhydride," Journal of Applied Polymer Science, vol. 103, Issue 3, pp. 2041-2048 (Feb. 5, 2007).

Liu, Y-L., et al., "Halogen-free flame retardant epoxy resins from hybrids of phosphorus- or silicon-containing epoxies with an amine resin," Journal of Applied Polymer Science, vol. 102, Issue 2, pp. 1071-1077 (Oct. 15, 2006).

Lubczak, J., "Polyhydroxyalkyl derivatives and polyetherols obtained from azacyclic compounds, Part II. Reactions with Formaldehyde and Alkylene Carbonates," Polimery, vol. 56, Issue 6, pp. 452-460 (2011).

Mann, S., "Self-assembly and transformation of hybrid nano-objects and nanostructures under equilibrium and non-equilibrium conditions," Nature Materials, vol. 8, Issue 10, pp. 781-792 (Sep. 6, 2009).

Pan et al., "Preparation of LMP302 Aromatic Polyester", Polyurethane Industry, No. 1, pp. 24-29 (Apr. 30, 1991).

Pedroso, L.M., et al., "Melamine/epichlorohydrin prepolymers: syntheses and characterization," Polymer, vol. 46, Issue 6, pp. 1766-1774 (Feb. 2005).

Pilato, L., "Resin Chemistry," Phenolic Resins: A Century of Progress, Chapter-4, pp. 41-91 (Feb. 27, 2010).

Rakhimova, E.B., et al., "New Methods for the Synthesis of $\alpha,\omega$-BIS-1,5,3-Dithiazepanes on the Basis of Aliphatic $\alpha,\omega$-Diamines," Chemistry of Heterocyclic Compounds, vol. 49, No. 8, pp. 1237-1242 (Aug. 2013).

Simon, J., "Coatings odds and ends—From pinch tests to trade shows," accessed at https://web.archive.org/web/20120826140533/http://info.biocoat.com/?Tag=hydrophilic+coating+market, Posted on Feb. 23, 2012, pp. 5.

Simon, J., "Lubricious Coatings in spec, on time, and on budget," accessed at https://web.archive.org/web/20120825102849/http://info.biocoat.com/?Tag=medical+device+coating, Posted on Aug. 13, 2012, pp. 6.

Swanson, J, O., et al., "Investigation of network development and properties in multifunctional epoxy resins using 3,3'-diaminodiphenylsulfone," accessed at http://www.trfa.org/Documents/Entry7-Swanson.pdf, accessed on Mar. 15, 2017, pp. 15.

Thring, R.W. "Catalytic Upgrading of a Solvolysis Lignin in a Batch Reactor," accessed at http://www.ciiq.org/varios/peru_2005/Trabajos/l/2/1.2.12.pdf, accessed on Mar. 15, 2017, pp. 17.

Xia, J., and Zana, R., "Applications of Gemini Surfactants," Gemini Surfactants: Synthesis, Interfacial and Solution-Phase Behavior, and Applications, 2nd Edition, vol. 117, Chapter 13, eds., Zana, R., and Xia, J., pp. 296-315 (2004).

Zaasshi, K.K., et al., "Formation of melamine and other cyanamide compounds by polymerization and condensation of dicyandiamide. IV. Proof of the formation of 2,4,6-trimethyl-s-triazine", Journal of the Society of Chemical Industry, vol. 71, No. 5, pp. 727-732 (May 31, 1968).

Fields, D.L., et al. "Mannich-type Condensation of Hydroquinone, Formaldehyde and Primary Amines," The Journal of Organic Chemistry, vol. 27, No. 8, pp. 2749-2753 (Aug. 1962).

Partial Supplementary European Search Report for European Application No. 13898534.6 dated Jun. 27, 2017, pp. 16.

MULTI-FUNCTIONAL PHENOLIC RESINS

CLAIM OF PRIORITY

This application is a U.S. national stage filing under 35 U.S.C. §371 of International Application No. PCT/US2013/045579 filed on Jun. 13, 2013 entitled "MULTI-FUNCTIONAL PHENOLIC RESINS," which is incorporated herein by reference in its entirety.

BACKGROUND

Over 6 million tons of phenolic resins are produced each year globally. They are relatively inexpensive and possess excellent properties, making them suitable for a wide range of applications. Phenolic resins exhibit good heat resistance, high mechanical strength, electrical insulation, excellent creep resistance, good processability, and flame resistance.

Phenol-formaldehyde resins generally occur in two forms: resole (viscous liquid) and novolac (solid). Resoles have a formaldehyde to phenol ratio of greater than one. Resoles are self-curing without requiring any cross-linkers, and can be easily compounded with additives, fillers, or fibers. Curing of resole occurs by the loss of 1.5 moles of formaldehyde per mole of resole, which is usually released as a toxic gas. The shelf-life of resole is 6-8 months when stabilized and stored under ideal conditions. Novolacs, on the other hand, have a formaldehyde-to-phenol molar ratio of less than one. Novolacs require curing agents and is usually mixed with hexamine derivatives.

Several curing agents for novolac resins are known in the art, including formaldehyde, paraformaldehyde and hexamethylenetetramine. The most common curing agent is hexamethylenetetramine, which reacts upon heating to yield ammonia, formaldehyde, methylene amine derivatives, and a cured resin. These curing agents complete the cross-linking reaction to convert a thermoplastic novolac resin to an insoluble infusible state. However, each of these novolac curing agents has certain disadvantages. For instance, where hexamethylenetetramine or formaldehyde are used to cure a novolac resin, volatile reaction products are emitted during the cure reaction. Specifically, when the curing agent is hexamethylenetetramine, toxic gas such as ammonia and formaldehyde are released during curing of the novolac resin. Further, hexamethylene derivatives are highly explosive, and require storing the cured resins under temperature regulated conditions, which are not economical. In addition, novolac curing agents like hexamethylenetetramine typically require curing temperatures as high as 150° C. Cure temperatures can be lowered by the addition of acids, but this often introduces other problems such as die staining, die sticking and sublimation of organic acids into the atmosphere.

Whilst both of these phenolic resins are used ubiquitously, the issues outlined above concerning their handling, storage and the necessary curing with dangerous chemicals creates an opportunity for improvements. Furthermore, it is possible to further enhance the physical, chemical and mechanical properties of these resins. Accordingly, there is a need for the production of new resins with enhanced functionality and improved safety which can be used in a wide variety of industrial applications.

SUMMARY

The present disclosure is directed to various phenolic resins and phenolic compounds with multi-functional groups. In one embodiment, a compound is of formula I

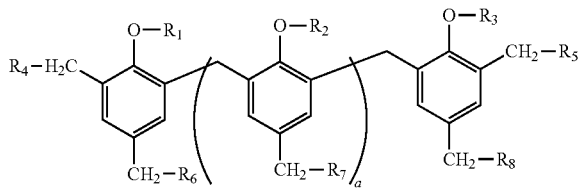

(I)

wherein:

a is an integer from 1 to 10;

$R_1$ is H, Z, —C(=O)—CH=CH$_2$, —(CH$_2$—CH$_2$—O)$_n$H, —(CH$_2$—CH$_2$—CH$_2$—O)$_n$H, or —(CH$_2$—CH$_2$—O)$_n$—(CH$_2$—CH(CH$_3$)—O)$_n$H, where each n is, independently, an integer from 1 to 18;

each $R_2$ is, independently, H, Z, —C(=O)—CH=CH$_2$, —(CH$_2$—CH$_2$—O)$_p$H, —(CH$_2$—CH$_2$—CH$_2$—O)$_p$H, or —(CH$_2$—CH$_2$—O)$_p$—(CH$_2$—CH(CH$_3$)—O)$_p$H, where each p is, independently, an integer from 1 to 18;

$R_3$ is H, Z, —C(=O)—CH=CH$_2$, —(CH$_2$—CH$_2$—O)$_q$H, —(CH$_2$—CH$_2$—CH$_2$—O)$_q$H, or —(CH$_2$—CH$_2$—O)$_q$—(CH$_2$—CH(CH$_3$)—O)$_q$H, where each q is, independently, an integer from 1 to 18;

$R_4$ is —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_r$—CH$_3$, —NH—Z, —N[CH$_2$O—C(=O)—CH=CH2]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_r$H, —(CH$_2$—CH$_2$—CH$_2$—O)$_r$H, —N[CH$_2$—CH$_2$—O—C(=O)—CH=CH$_2$]$_2$, or —N[CH$_2$—CH$_2$—NH—C(=O)—CH=CH$_2$]$_2$, where r is an integer from 1 to 18;

$R_5$ is —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O- (alkylene)-CH$_3$, —CH$_2$—Y, —NCO, —O—C(=O)—(CH$_2$)$_t$—CH$_3$, —NH—Z, —N[CH$_2$O—C(=O)—CH=CH2]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_t$H, —(CH$_2$—CH$_2$—CH$_2$—O)$_t$H, —N[CH$_2$—CH$_2$—O—C(=O)—CH=CH$_2$]$_2$, or —N[CH$_2$—CH$_2$—NH—C(=O)—CH=CH$_2$]$_2$, where t is an integer from 1 to 18;

$R_6$ is —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_v$—CH$_3$, —NH—Z, —N[CH$_2$O—C(=O)—CH=CH2]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_v$H, —(CH$_2$—CH$_2$—CH$_2$—O)$_v$H, —N[CH$_2$—CH$_2$—O—C(=O)—CH=CH$_2$]$_2$, or —N[CH$_2$—CH$_2$—NH—C(=O)—CH=CH$_2$]$_2$, where v is an integer from 1 to 18;

each $R_7$ is, independently, —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_w$—CH$_3$, —NH—Z, —N[CH$_2$O—C(=O)—CH=CH2]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_w$H, —(CH$_2$—CH$_2$—CH$_2$—O)$_w$H, —N[CH$_2$—CH$_2$—O—C(=O)—CH=CH$_2$]$_2$, or —N[CH$_2$—CH$_2$—NH—C(=O)—CH=CH$_2$]$_2$, where w is an integer from 1 to 18;

R$_8$ is —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O- (alkylene)-CH$_3$, —CH$_2$—Y, —NCO, —O—C(=O)—(CH$_2$)$_x$—CH$_3$, —NH—Z, —N[CH$_2$O—C(=O)—CH=CH2]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_x$H, —(CH$_2$—CH$_2$—CH$_2$—O)$_x$H, —N[CH$_2$—CH$_2$—O—C(=O)—CH=CH$_2$]$_2$, or —N[CH$_2$—CH$_2$—NH—C(=O)—CH=CH$_2$]$_2$, where x is an integer from 1 to 18;

Z is

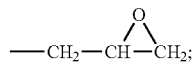

and

Y is Cl, Br, F, or I.

In an additional embodiment, a composition may include any one or more of the compounds of formula I as described herein. In some embodiments, the composition may be or include an absorbent polymer, or a carbon fiber resin comprising any one or more of the compounds of formula I as described herein. In a further embodiment, an article may include any one or more of the compounds of formula I as described herein. In a further embodiment, a resin may include any one or more of the compounds of formula I as described herein.

In a further embodiment, methods of preparing a compound may include: contacting a novolac compound with a formaldehyde or paraformaldehyde to form a hydroxymethyl compound; and contacting the hydroxymethyl compound with an epihalohydrin, an acrylic compound, an alkanoyl halide, an alkyl halide, ammonia, phosgene, or a dialkylamine to form the compound.

In an additional embodiment, a method to enhance thermal stability, glass transition temperature or chemical resistance of a resin may include incorporating any one or more of the compounds of formula I as described herein in the resin.

DETAILED DESCRIPTION

Figure 1:
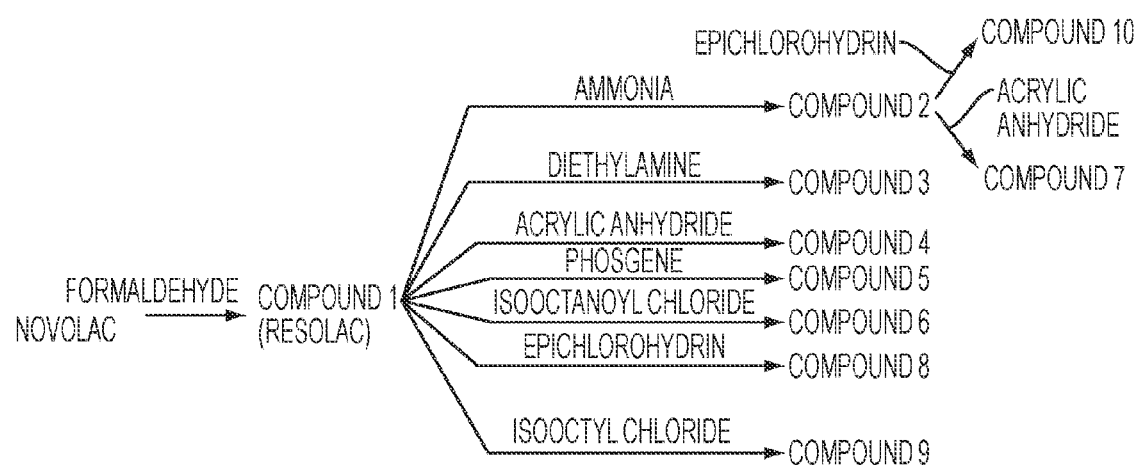
FIG. 1 illustrates reaction steps according to an embodiment.

This disclosure is not limited to the particular systems, devices and methods described, as these may vary. The terminology used in the description is for the purpose of describing the particular versions or embodiments only, and is not intended to limit the scope.

As used herein, "alkylene" refers to a bivalent alkyl moiety having the general formula —(CH$_2$)$_n$—, where n is from about 1 to about 25, about 1 to about 20, or about 4 to about 20. By bivalent, it is meant that the group has two open sites each of which bonds to another group. Non-limiting examples include, but are not limited to, methylene, ethylene, trimethylene, pentamethylene, and hexamethylene. Alkylene groups can be substituted or unsubstituted, linear or a branched bivalent alkyl groups.

As used herein, the term "alkyl" refers to a saturated hydrocarbon group which is straight-chained or branched. An alkyl group can contain from 1 to 20 carbon atoms, from 2 to 20 carbon atoms, from 1 to 10 carbon atoms, from 2 to 10 carbon atoms, from 1 to 8 carbon atoms, from 2 to 8 carbon atoms, from 1 to 6 carbon atoms, from 2 to 6 carbon atoms, from 1 to 4 carbon atoms, from 2 to 4 carbon atoms, from 1 to 3 carbon atoms, or 2 carbon atoms, or 3 carbon atoms. Examples of alkyl groups include, but are not limited to, methyl (Me), ethyl (Et), propyl (example, n-propyl and isopropyl), butyl (example, n-butyl, t-butyl, isobutyl), pentyl (example, n-pentyl, isopentyl, neopentyl), hexyl, isohexyl, heptyl, 4,4 dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

Disclosed herein are compositions and methods for making various phenolic resins and compounds with multifunctional groups. In some embodiments, the phenolic compound is of formula I:

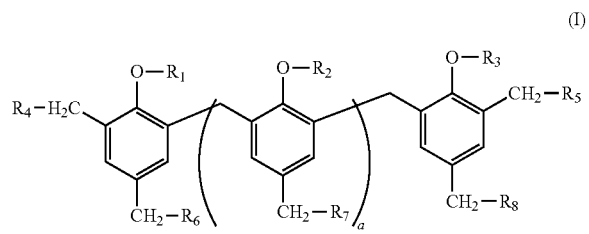

(I)

wherein:

a is an integer from 1 to 10;

R$_1$ is H, Z, —C(=O)—CH=CH$_2$, —(CH$_2$—CH$_2$—O)$_n$H, —(CH$_2$—CH$_2$—CH$_2$—O)$_n$H, or —(CH$_2$—CH$_2$—

O)$_n$—(CH$_2$—CH(CH$_3$)—O)$_n$H, where each n is, independently, an integer from 1 to 18;

each R$_2$ is, independently, H, Z, —C(=O)—CH=CH$_2$, —(CH$_2$—CH$_2$—O)$_p$H, —(CH$_2$—CH$_2$—CH$_2$—O)$_p$H, or —(CH$_2$—CH$_2$—O)$_p$—(CH$_2$—CH(CH$_3$)—O)$_p$H, where each p is, independently, an integer from 1 to 18;

R$_3$ is H, Z, —C(=O)—CH=CH$_2$, —(CH$_2$—CH$_2$—O)$_q$H, —(CH$_2$—CH$_2$—CH$_2$—O)$_q$H, or —(CH$_2$—CH$_2$—O)$_q$—(CH$_2$—CH(CH$_3$)—O)$_q$H, where each q is, independently, an integer from 1 to 18;

R$_4$ is —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_r$—CH$_3$, —NH—Z, —N[CH$_2$O—C(=O)—CH=CH2]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_r$H, —(CH$_2$—CH$_2$—CH$_2$—O)$_r$H, —N[CH$_2$—CH$_2$—O—C(=O)—CH=CH$_2$]$_2$, or —N[CH$_2$—CH$_2$—NH—C(=O)—CH=CH$_2$]$_2$, where r is an integer from 1 to 18;

R$_5$ is —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_t$—CH$_3$, —NH—Z, —N[CH$_2$O—C(=O)—CH=CH2]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_t$H, —(CH$_2$—CH$_2$—CH$_2$—O)$_t$H, —N[CH$_2$—CH$_2$—O—C(=O)—CH=CH$_2$]$_2$, or —N[CH$_2$—CH$_2$—NH—C(=O)—CH=CH$_2$]$_2$, where t is an integer from 1 to 18;

R$_6$ is —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_v$—CH$_3$, —NH—Z, —N[CH$_2$O—C(=O)—CH=CH2]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_v$H, —(CH$_2$—CH$_2$—CH$_2$—O)$_v$H, —N[CH$_2$—CH$_2$—O—C(=O)—CH=CH$_2$]$_2$, or —N[CH$_2$—CH$_2$—NH—C(=O)—CH=CH$_2$]$_2$, where v is an integer from 1 to 18;

each R$_7$ is, independently, —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_w$—CH$_3$, —NH—Z, —N[CH$_2$O—C(=O)—CH=CH2]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_w$H, —(CH$_2$—CH$_2$—CH$_2$—O)$_w$H, —N[CH$_2$—CH$_2$—O—C(=O)—CH=CH$_2$]$_2$, or —N[CH$_2$—CH$_2$—NH—C(=O)—CH=CH$_2$]$_2$, where w is an integer from 1 to 18;

R$_8$ is —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_x$—CH$_3$, —NH—Z, —N[CH$_2$O—C(=O)—CH=CH2]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_x$H, —(CH$_2$—CH$_2$—CH$_2$—O)$_x$H, —N[CH$_2$—CH$_2$—O—C(=O)—CH=CH$_2$]$_2$, or —N[CH$_2$—CH$_2$—NH—C(=O)—CH=CH$_2$]$_2$, where x is an integer from 1 to 18;

Z is

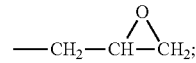

and

Y is Cl, Br, F, or I.

In some embodiments, a is an integer from 1 to 5, an integer from 1 to 3 or an integer from 3 to 5. In some embodiments, a is 1. In some embodiments, a is 5.

In some embodiments, R$_1$ may be H, Z, —C(=O)—CH=CH$_2$, —(CH$_2$—CH$_2$—O)$_n$H, —(CH$_2$—CH$_2$—CH$_2$—O)$_n$H, or —(CH$_2$—CH$_2$—O)$_n$—(CH$_2$—CH(CH$_3$)—O)$_n$H, where each n is, independently, an integer from 1 to 18. In some embodiments, R$_1$ may be H, Z, or —C(=O)—CH=CH$_2$, —(CH$_2$—CH$_2$—O)$_n$H.

In some embodiments, each R$_2$ may be H, Z, —C(=O)—CH=CH$_2$, —(CH$_2$—CH$_2$—O)$_p$H, —(CH$_2$—CH$_2$—CH$_2$—O)$_p$H, or —(CH$_2$—CH$_2$—O)$_p$—(CH$_2$—CH(CH$_3$)—O)$_p$H, where each p is, independently, an integer from 1 to 18. In some embodiments, each R$_2$ may be H, Z, —C(=O)—CH=CH$_2$, or —(CH$_2$—CH$_2$—O)$_p$H.

In some embodiments, R$_3$ may be H, Z, —C(=O)—CH=CH$_2$, —(CH$_2$—CH$_2$—O)$_q$H, (CH$_2$—CH$_2$—CH$_2$—O)$_q$H, or —(CH$_2$—CH$_2$—O)$_q$—(CH$_2$—CH(CH$_3$)—O)$_q$H, where each q is, independently, an integer from 1 to 18. In some embodiments, R$_3$ may be H, Z, —C(=O)—CH=CH$_2$, —(CH$_2$—CH$_2$—O)$_q$H.

In some embodiments, R$_4$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_r$—CH$_3$, —NH—Z, —N[CH$_2$O—C(=O)—CH=CH$_2$]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_r$H, —(CH$_2$—CH$_2$—CH$_2$—O)$_r$H, —N[CH$_2$—CH$_2$—O—C(=O)—CH=CH$_2$]$_2$, or —N[CH$_2$—CH$_2$—NH—C(=O)—CH=CH$_2$]$_2$, where r is an integer from 1 to 18. In some embodiments, R$_4$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O- (alkylene)-CH$_3$, —CH$_2$—Y, —NCO, —O—C(=O)—(CH$_2$)$_r$—CH$_3$, —NH—Z, —N[CH$_2$O—C(=O)—CH=CH$_2$]$_2$, —NH—C(=O)CH=CH$_2$, —CH$_2$CH$_2$—O—Z, —CH$_2$CH$_2$OH, —O—C(=O)—CH=CH$_2$, or —N(CH$_2$—CH$_2$—NH$_2$)$_2$. In some embodiments, R$_4$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_r$—CH$_3$, —NH—Z, —N[CH$_2$O—C(=O)—CH=CH$_2$]$_2$, or —NH—C(=O)CH=CH$_2$.

In some embodiments, R$_5$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_t$—CH$_3$, —NH—Z, —N[CH$_2$O—C(=O)—CH=CH$_2$]$_2$, —NH—C(=O)CH=CH$_2$, —CH$_2$CH$_2$—O—Z, —CH$_2$CH$_2$OH, —O—C (=O)—CH=CH$_2$, —N(CH$_2$—CH$_2$—NH$_2$)$_2$, —(CH$_2$—CH$_2$—O)$_t$H, —(CH$_2$—CH$_2$—CH$_2$—O)$_t$H, —N[CH$_2$—CH$_2$—O—C(=O)—CH=CH$_2$]$_2$, or —N[CH$_2$—CH$_2$—NH—C(=O)—CH=CH$_2$]$_2$, where t is an integer from 1 to 18. In some embodiments, R$_5$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_t$—CH$_3$, —NH—Z, —N[CH$_2$O—C(=O)—CH=CH$_2$]$_2$, —NH—C(=O)CH=CH$_2$, —CH$_2$CH$_2$—O—Z, —CH$_2$CH$_2$OH, —O—C(=O)—CH=CH$_2$, or —N(CH$_2$—CH$_2$—NH$_2$)$_2$. In some embodiments, R$_5$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_t$—CH$_3$, —NH—Z, —N[CH$_2$O—C(=O)—CH=CH$_2$]$_2$, or —NH—C(=O)CH=CH$_2$.

In some embodiments, R$_6$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_v$—CH$_3$, —NH—Z, —N[CH$_2$O—C(=O)—CH=CH$_2$]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_v$H, —(CH$_2$—CH$_2$—CH$_2$—O)$_v$H, —N[CH$_2$—CH$_2$—O—C(=O)—CH=CH$_2$]$_2$, or —N[CH$_2$—CH$_2$—NH—C(=O)—CH=CH$_2$]$_2$, where v is an integer from 1 to 18.

In some embodiments, R$_6$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_v$—CH$_3$, —N[CH$_2$O—C(=O)—CH=CH$_2$]$_2$, —NH—C(=O)CH=CH$_2$, —CH$_2$CH$_2$—O—Z, —CH$_2$CH$_2$OH, —O—C(=O)—CH=CH$_2$, or —N(CH$_2$—CH$_2$—NH$_2$)$_2$. In some embodiments, R$_6$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_v$—CH$_3$, —NH—Z, or —N[CH$_2$O—C(=O)—CH=CH$_2$]$_2$.

In some embodiments, each R$_7$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_w$—CH$_3$, —NH—Z, —N[CH$_2$O—C(=O)—CH=CH$_2$]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_w$H, —(CH$_2$—CH$_2$—CH$_2$—O)$_w$H, —N[CH$_2$—CH$_2$—O—C(=O)—CH=CH$_2$]$_2$, or —N[CH$_2$—CH$_2$—NH—C(=O)—CH=CH$_2$]$_2$, where w is an integer from 1 to 18. In some embodiments, each R$_7$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_w$—CH$_3$, —NH—Z, —N[CH$_2$O—C(=O)—CH=CH2]$_2$, —NH—C(=O)CH=CH$_2$, —CH$_2$CH$_2$—O—Z, —CH$_2$CH$_2$OH, —O—C(=O)—CH=CH$_2$, or —N(CH$_2$—CH$_2$—NH$_2$)$_2$. In some embodiments, each R$_7$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_w$—CH$_3$, —NH—Z, —N[CH$_2$O—C(=O)—CH=CH$_2$]$_2$, or —NH—C(=O)CH=CH$_2$.

In some embodiments, R$_8$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_x$—CH$_3$, —NH—Z, —N[CH$_2$O—C(=O)—CH=CH$_2$]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_x$H, —(CH$_2$—CH$_2$—CH$_2$—O)$_x$H, —N[CH$_2$—CH$_2$—O—C(=O)—CH=CH$_2$]$_2$, or —N[CH$_2$—CH$_2$—NH—C(=O)—CH=CH$_2$]$_2$, where x is an integer from 1 to 18. In some embodiments, R$_8$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_x$—CH$_3$, —NH—Z, —N[CH$_2$O—C(=O)—CH=CH$_2$]$_2$, —NH—C(=O)CH=CH$_2$, —CH$_2$CH$_2$—O—Z, —CH$_2$CH$_2$OH, —O—C(=O)—CH=CH$_2$, or —N(CH$_2$—CH$_2$—NH$_2$)$_2$. In some embodiments, R$_8$ may be —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_x$—CH$_3$, —NH—Z, —N[CH$_2$O—C(=O)—CH=CH$_2$]$_2$, or —NH—C(=O)CH=CH$_2$.

In some embodiments, Z is

—CH$_2$—CH(—O—)CH$_2$;

In some embodiments, Y is Cl, Br, F, or I.

In some embodiments, compounds of formula I may have the following substitutions at each of, independently, R$_1$, R$_2$, R$_3$, R$_4$, R$_5$, R$_6$, R$_7$, and R$_8$ as shown in Table 1.

TABLE 1

| R$_1$ | R$_2$ | R$_3$ |
|---|---|---|
| H, | H, | H, |
| Z, | Z, | Z, |
| —C(=O)—CH=CH$_2$, | —C(=O)—CH=CH$_2$, | —C(=O)—CH=CH$_2$, |
| —(CH$_2$—CH$_2$—O)$_n$H, | —(CH$_2$—CH$_2$—O)$_p$H, | —(CH$_2$—CH$_2$—O)$_q$H, |
| —(CH$_2$—CH$_2$—CH$_2$—O)$_n$H, | —(CH$_2$—CH$_2$—CH$_2$—O)$_p$H, | —(CH$_2$—CH$_2$—CH$_2$—O)$_q$H, |

TABLE 1-continued

| | | |
|---|---|---|
| or<br>—(CH$_2$—CH$_2$—O)$_n$—(CH$_2$—CH(CH$_3$)—O)$_n$H,<br>where each n is independently, an integer from 1 to 18. | or<br>—(CH$_2$—CH$_2$—O)$_p$—(CH$_2$—CH(CH$_3$)—O)$_p$H,<br>where each p is independently, an integer from 1 to 18. | or<br>—(CH$_2$—CH$_2$—O)$_q$—(CH$_2$—CH(CH$_3$)—O)$_q$H,<br>where each q is independently, an integer from 1 to 18. |
| Z,<br>—C(=O)—CH=CH$_2$,<br>or<br>—(CH$_2$—CH$_2$—O)$_n$H. | Z,<br>—C(=O)—CH=CH$_2$,<br>or<br>—(CH$_2$—CH$_2$—O)$_p$H. | Z,<br>—C(=O)—CH=CH$_2$,<br>or<br>—(CH$_2$—CH$_2$—O)$_q$H. |
| H,<br>Z, or<br>—C(=O)—CH=CH$_2$. | H,<br>Z, or<br>—C(=O)—CH=CH$_2$. | H,<br>Z, or<br>—C(=O)—CH=CH$_2$. |
| —C(=O)—CH=CH$_2$,<br>or<br>—(CH$_2$—CH$_2$—O)$_n$H. | —C(=O)—CH=CH$_2$,<br>or<br>—(CH$_2$—CH$_2$—O)$_p$H. | —C(=O)—CH=CH$_2$,<br>or<br>—(CH$_2$—CH$_2$—O)$_q$H. |
| —C(=O)—CH=CH$_2$,<br>or<br>—(CH$_2$—CH$_2$—O)$_n$H. | —C(=O)—CH=CH$_2$,<br>or<br>—(CH$_2$—CH$_2$—O)$_p$H. | —C(=O)—CH=CH$_2$,<br>or<br>—(CH$_2$—CH$_2$—O)$_q$H. |
| —(CH$_2$—CH$_2$—O)$_n$—(CH$_2$—CH(CH$_3$)—O)$_n$H<br>—C(=O)—CH=CH$_2$<br>or<br>—(CH$_2$—CH$_2$—O)$_n$H. | —(CH$_2$—CH$_2$—O)$_n$—(CH$_2$—CH(CH$_3$)—O)$_p$H<br>—C(=O)—CH=CH$_2$<br>or<br>—(CH$_2$—CH$_2$—O)$_p$H. | —(CH$_2$—CH$_2$—O)$_n$—(CH$_2$—CH(CH$_3$)—O)$_q$H<br>—C(=O)—CH=CH$_2$<br>or<br>—(CH$_2$—CH$_2$—O)$_q$H. |
| H | H | H |
| H | H | H |
| Z | Z | Z |
| H | H | H |
| H | H | H |
| H | H | H |
| H | H | H |
| H | H | H |
| Z | Z | Z |
| —(CH$_2$—CH$_2$—O)$_n$—(CH$_2$—CH(CH$_3$)—O)$_n$H | —(CH$_2$—CH$_2$—O)$_p$—(CH$_2$—CH(CH$_3$)—O)$_p$H | —(CH$_2$—CH$_2$—O)$_q$—(CH$_2$—CH(CH$_3$)—O)$_q$H |
| Z | Z | Z |

| R$_4$ | R$_5$ | R$_6$ |
|---|---|---|
| —OH,<br>—NH$_2$,<br>—O—Z,<br>—N(Z)$_2$,<br>—N(CH$_2$—O—Z)$_2$,<br>—N(CH$_2$OH)$_2$,<br>—N(CH$_2$CH$_2$—O—Z)$_2$,<br>—N(CH$_2$NH$_2$)$_2$,<br>—N(CH$_2$CH$_2$OH)$_2$,<br>—CH$_2$—O—Z,<br>—CH$_2$—OH,<br>—CH$_2$—NH$_2$,<br>—N(CH$_3$)$_2$,<br>—O-(alkylene)—CH$_3$,<br>—CH$_2$—Y,<br>—NCO,<br>—O—C(=O)—(CH$_2$)$_r$—CH$_3$,<br>—NH—Z,<br>—N[CH$_2$O—C(=O)—CH=CH$_2$]$_2$,<br>—NH—C(=O)CH=CH$_2$,<br>—CH$_2$CH$_2$—O—Z,<br>—CH$_2$CH$_2$OH,<br>—O—C(=O)—CH=CH$_2$,<br>—N(CH$_2$—CH$_2$—NH$_2$)$_2$,<br>—(CH$_2$—CH$_2$—O)$_r$H,<br>—(CH$_2$—CH$_2$—CH$_2$—O)$_r$H,<br>—N[CH$_2$—CH$_2$—O—C(=O)—CH=CH$_2$]$_2$,<br>or<br>—N[CH$_2$—CH$_2$—NH—C(=O)—CH=CH$_2$]$_2$,<br>where r is an integer from 1 to 18.<br>—NH$_2$,<br>—N(CH$_3$)$_2$,<br>—O—C(=O)—CH=CH$_2$,<br>—NCO,<br>—O—C(=O)—(CH$_2$)$_r$—CH$_3$,<br>—NH—C(=O)CH=CH$_2$, | —OH,<br>—NH$_2$,<br>—O—Z,<br>—N(Z)$_2$,<br>—N(CH$_2$—O—Z)$_2$,<br>—N(CH$_2$OH)$_2$,<br>—N(CH$_2$CH$_2$—O—Z)$_2$,<br>—N(CH$_2$NH$_2$)$_2$,<br>—N(CH$_2$CH$_2$OH)$_2$,<br>—CH$_2$—O—Z,<br>—CH$_2$—OH,<br>—CH$_2$—NH$_2$,<br>—N(CH$_3$)$_2$,<br>—O-(alkylene)—CH$_3$,<br>—CH$_2$—Y,<br>—NCO,<br>—O—C(=O)—(CH$_2$)$_t$—CH$_3$,<br>—NH—Z,<br>—N[CH$_2$O—C(=O)—CH=CH$_2$]$_2$,<br>—NH—C(=O)CH=CH$_2$,<br>—CH$_2$CH$_2$—O—Z,<br>—CH$_2$CH$_2$OH,<br>—O—C(=O)—CH=CH$_2$,<br>—N(CH$_2$—CH$_2$—NH$_2$)$_2$,<br>—(CH$_2$—CH$_2$—O)$_t$H,<br>—(CH$_2$—CH$_2$—CH$_2$—O)$_t$H,<br>—N[CH$_2$—CH$_2$—O—C(=O)—CH=CH$_2$]$_2$,<br>or<br>—N[CH$_2$—CH$_2$—NH—C(=O)—CH=CH$_2$]$_2$,<br>where t is an integer from 1 to 18.<br>—NH$_2$,<br>—N(CH$_3$)$_2$,<br>—O—C(=O)—CH=CH$_2$,<br>—NCO,<br>—O—C(=O)—(CH$_2$)$_t$—CH$_3$,<br>—NH—C(=O)CH=CH$_2$, | —OH,<br>—NH$_2$,<br>—O—Z,<br>—N(Z)$_2$,<br>—N(CH$_2$—O—Z)$_2$,<br>—N(CH$_2$OH)$_2$,<br>—N(CH$_2$CH$_2$—O—Z)$_2$,<br>—N(CH$_2$NH$_2$)$_2$,<br>—N(CH$_2$CH$_2$OH)$_2$,<br>—CH$_2$—O—Z,<br>—CH$_2$—OH,<br>—CH$_2$—NH$_2$,<br>—N(CH$_3$)$_2$,<br>—O-(alkylene)—CH$_3$,<br>—CH$_2$—Y,<br>—NCO,<br>—O—C(=O)—(CH$_2$)$_v$—CH$_3$,<br>—NH—Z,<br>—N[CH$_2$O—C(=O)—CH=CH$_2$]$_2$,<br>—NH—C(=O)CH=CH$_2$,<br>—CH$_2$CH$_2$—O—Z,<br>—CH$_2$CH$_2$OH,<br>—O—C(=O)—CH=CH$_2$,<br>—N(CH$_2$—CH$_2$—NH$_2$)$_2$,<br>—(CH$_2$—CH$_2$—O)$_v$H,<br>—(CH$_2$—CH$_2$—CH$_2$—O)$_v$H,<br>—N[CH$_2$—CH$_2$—O—C(=O)—CH=CH$_2$]$_2$,<br>or<br>—N[CH$_2$—CH$_2$—NH—C(=O)—CH=CH$_2$]$_2$,<br>where v is an integer from 1 to 18.<br>—NH$_2$,<br>—N(CH$_3$)$_2$,<br>—O—C(=O)—CH=CH$_2$,<br>—NCO,<br>—O—C(=O)—(CH$_2$)$_v$—CH$_3$,<br>—NH—C(=O)CH=CH$_2$, |

TABLE 1-continued

| | | |
|---|---|---|
| —O—Z, | —O—Z, | —O—Z, |
| —O—(CH$_2$)$_7$—CH$_3$, | —O—(CH$_2$)$_7$—CH$_3$, | —O—(CH$_2$)$_7$—CH$_3$, |
| —NH—Z, or | —NH—Z, or | —NH—Z, or |
| —N(CH$_2$—CH$_2$—OH)$_2$. | —N(CH$_2$—CH$_2$—OH)$_2$. | —N(CH$_2$—CH$_2$—OH)$_2$. |
| —OH, | —OH, | —OH, |
| —NH$_2$, | —NH$_2$, | —NH$_2$, |
| —O—Z, | —O—Z, | —O—Z, |
| —N(Z)$_2$, | —N(Z)$_2$, | —N(Z)$_2$, |
| —N(CH$_2$—O—Z)$_2$, | —N(CH$_2$—O—Z)$_2$, | —N(CH$_2$—O—Z)$_2$, |
| or | or | or |
| —N(CH$_2$OH)$_2$. | —N(CH$_2$OH)$_2$. | —N(CH$_2$OH)$_2$. |
| —N(Z)$_2$, | —N(Z)$_2$, | —N(Z)$_2$, |
| —N(CH$_2$CH$_2$—O—Z)$_2$, | —N(CH$_2$CH$_2$—O—Z)$_2$, | —N(CH$_2$CH$_2$—O—Z)$_2$, |
| —N(CH$_2$CH$_2$—NH$_2$)$_2$, | —N(CH$_2$CH$_2$—NH$_2$)$_2$, | —N(CH$_2$CH$_2$—NH$_2$)$_2$, |
| or | or | or |
| —O—C(=O)—CH=CH$_2$. | —O—C(=O)—CH=CH$_2$. | —O—C(=O)—CH=CH$_2$. |
| —N(CH$_2$CH$_2$—O—Z)$_2$, | —N(CH$_2$CH$_2$—O—Z)$_2$, | —N(CH$_2$CH$_2$—O—Z)$_2$, |
| —N(CH$_2$NH$_2$)$_2$, | —N(CH$_2$NH$_2$)$_2$, | —N(CH$_2$NH$_2$)$_2$, |
| —N(CH$_2$CH$_2$OH)$_2$, | —N(CH$_2$CH$_2$OH)$_2$, | —N(CH$_2$CH$_2$OH)$_2$, |
| —CH$_2$—O—Z, | —CH$_2$—O—Z, | —CH$_2$—O—Z, |
| —CH$_2$—OH, | —CH$_2$—OH, | —CH$_2$—OH, |
| —CH$_2$—NH$_2$, | —CH$_2$—NH$_2$, | —CH$_2$—NH$_2$, |
| —N(CH$_3$)$_2$, | —N(CH$_3$)$_2$, | —N(CH$_3$)$_2$, |
| —O- | —O- | —O- |
| (alkylene) —CH$_3$, | (alkylene) —CH$_3$, | (alkylene) —CH$_3$, |
| or | or | or |
| —CH$_2$—Y. | —CH$_2$—Y. | —CH$_2$—Y. |
| —NCO, | —NCO, | —NCO, |
| —O—C(=O)—(CH$_2$)$_r$—CH$_3$, | —O—C(=O)—(CH$_2$)$_t$—CH$_3$, | —O—C(=O)—(CH$_2$)$_v$—CH$_3$, |
| —NH—Z, | —NH—Z, | —NH—Z, |
| —N[CH$_2$O—C(=O)—CH=CH$_2$]$_2$, | —N[CH$_2$O—C(=O)—CH=CH$_2$]$_2$, | —N[CH$_2$O—C(=O)—CH=CH$_2$]$_2$, |
| —NH—C(=O)CH=CH$_2$, | —NH—C(=O)CH=CH$_2$, | —NH—C(=O)CH=CH$_2$, |
| —CH$_2$CH$_2$—O—Z, | —CH$_2$CH$_2$—O—Z, | —CH$_2$CH$_2$—O—Z, |
| or | or | or |
| —CH$_2$CH$_2$OH. | —CH$_2$CH$_2$OH. | —CH$_2$CH$_2$OH. |
| —N(Z)$_2$, | —N(Z)$_2$, | —N(Z)$_2$, |
| —N(CH$_2$—O—Z)$_2$, | —N(CH$_2$—O—Z)$_2$, | —N(CH$_2$—O—Z)$_2$, |
| —N(CH$_2$—CH$_2$—NH$_2$)$_2$ | —N(CH$_2$—CH$_2$—NH$_2$)$_2$ | —N(CH$_2$—CH$_2$—NH$_2$)$_2$ |
| or | or | or |
| —O—C(=O)—CH=CH$_2$. | —O—C(=O)—CH=CH$_2$. | —O—C(=O)—CH=CH$_2$. |
| —O—C(=O)—CH=CH$_2$ | —O—C(=O)—CH=CH$_2$ | —O—C(=O)—CH=CH$_2$ |
| —N(CH$_3$)$_2$ | —N(CH$_3$)$_2$ | —N(CH$_3$)$_2$ |
| —O—Z | —O—Z | —O—Z |
| —NH$_2$ | —NH$_2$ | —NH$_2$ |
| —NCO | —NCO | —NCO |
| —O—C(=O)—(CH$_2$)$_6$—CH$_3$ | —O—C(=O)—(CH$_2$)$_6$—CH$_3$ | —O—C(=O)—(CH$_2$)$_6$—CH$_3$ |
| —NH—C(=O)CH=CH$_2$ | —NH—C(=O)CH=CH$_2$ | —NH—C(=O)CH=CH$_2$ |
| —O—(CH$_2$)$_7$—CH$_3$ | —O—(CH$_2$)$_7$—CH$_3$ | —O—(CH$_2$)$_7$—CH$_3$ |
| —NH—Z | —NH—Z | —NH—Z |
| —N(CH$_2$CH$_2$OH)$_2$ | —N(CH$_2$CH$_2$OH)$_2$ | —N(CH$_2$CH$_2$OH)$_2$ |
| —NCO | —NCO | —NCO |

| | $R_7$ | $R_8$ |
|---|---|---|
| | —OH, | —OH, |
| | —NH$_2$, | —NH$_2$, |
| | —O—Z, | —O—Z, |
| | —N(Z)$_2$, | —N(Z)$_2$, |
| | —N(CH$_2$—O—Z)$_2$, | —N(CH$_2$—O—Z)$_2$, |
| | —N(CH$_2$OH)$_2$, | —N(CH$_2$OH)$_2$, |
| | —N(CH$_2$CH$_2$—O—Z)$_2$, | —N(CH$_2$CH$_2$—O—Z)$_2$, |
| | —N(CH$_2$NH$_2$)$_2$, | —N(CH$_2$NH$_2$)$_2$, |
| | —N(CH$_2$CH$_2$OH)$_2$, | —N(CH$_2$CH$_2$OH)$_2$, |
| | —CH$_2$—O—Z, | —CH$_2$—O—Z, |
| | —CH$_2$—OH, | —CH$_2$—OH, |
| | —CH$_2$—NH$_2$, | —CH$_2$—NH$_2$, |
| | —N(CH$_3$)$_2$, | —N(CH$_3$)$_2$, |
| | —O- | —O- |
| | (alkylene) —CH$_3$, | (alkylene) —CH$_3$, |
| | —CH$_2$—Y, | —CH$_2$—Y, |
| | —NCO, | —NCO, |
| | —O—C(=O)—(CH$_2$)$_w$—CH$_3$, | —O—C(=O)—(CH$_2$)$_x$—CH$_3$, |
| | —NH—Z, | —NH—Z, |
| | —N[CH$_2$O—C(=O)—CH=CH$_2$]$_2$, | —N[CH$_2$O—C(=O)—CH=CH$_2$]$_2$, |
| | —NH—C(=O)CH=CH$_2$, | —NH—C(=O)CH=CH$_2$, |
| | —CH$_2$CH$_2$—O—Z, | —CH$_2$CH$_2$—O—Z, |
| | —CH$_2$CH$_2$OH, | —CH$_2$CH$_2$OH, |
| | —O—C(=O)—CH=CH$_2$, | —O—C(=O)—CH=CH$_2$, |
| | —N(CH$_2$—CH$_2$—NH$_2$)$_2$, | —N(CH$_2$—CH$_2$—NH$_2$)$_2$, |
| | —(CH$_2$—CH$_2$—O)$_w$H, | —(CH$_2$—CH$_2$—O)$_x$H, |

TABLE 1-continued

| | |
|---|---|
| —(CH$_2$—CH$_2$—CH$_2$—O)$_w$H, <br>—N[CH$_2$—CH$_2$—O—C(=O)—CH=CH$_2$]$_2$, <br>or <br>—N[CH$_2$—CH$_2$—NH—C(=O)—CH=CH$_2$]$_2$, <br>where w is an integer from 1 to 18. <br>—NH$_2$, <br>—N(CH$_3$)$_2$, <br>—O—C(=O)—CH=CH$_2$, <br>—NCO, <br>—O—C(=O)—(CH$_2$)$_w$—CH$_3$, <br>—NH—C(=O)CH=CH$_2$, <br>—O—Z, <br>—O—(CH$_2$)$_7$—CH$_3$, <br>—NH—Z, or <br>—N(CH$_2$—CH$_2$—OH)$_2$. <br>—OH, <br>—NH$_2$, <br>—O—Z, <br>—N(Z)$_2$, <br>—N(CH$_2$—O—Z)$_2$, <br>or <br>—N(CH$_2$OH)$_2$. <br>—N(Z)$_2$, <br>—N(CH$_2$CH$_2$—O—Z)$_2$, <br>—N(CH$_2$CH$_2$—NH$_2$)$_2$, <br>or <br>—O—C(=O)—CH—CH$_2$. <br>—N(CH$_2$CH$_2$—O—Z)$_2$, <br>—N(CH$_2$NH$_2$)$_2$, <br>—N(CH$_2$CH$_2$OH)$_2$, <br>—CH$_2$—O—Z, <br>—CH$_2$—OH, <br>—CH$_2$—NH$_2$, <br>—N(CH$_3$)$_2$, <br>—O-(alkylene)—CH$_3$, <br>or <br>—CH$_2$—Y. <br>—NCO, <br>—O—C(=O)—(CH$_2$)$_w$—CH$_3$, <br>—NH—Z, <br>—N[CH$_2$O—C(=O)—CH=CH$_2$]$_2$, <br>—NH—C(=O)CH=CH$_2$, <br>—CH$_2$CH$_2$—O—Z, <br>or <br>—CH$_2$CH$_2$OH. <br>—N(Z)$_2$, <br>—N(CH$_2$—O—Z)$_2$, <br>—N(CH$_2$—CH$_2$—NH$_2$)$_2$ <br>or <br>—O—C(=O)—CH=CH$_2$. <br>—O—C(=O)—CH=CH$_2$ <br>—N(CH$_3$)$_2$ <br>—O—Z <br>—NH$_2$ <br>—NCO <br>—O—C(=O)—(CH$_2$)$_6$—CH$_3$ <br>—NH—C(=O)CH=CH$_2$ <br>—O—(CH$_2$)$_7$—CH$_3$ <br>—NH—Z <br>—N(CH$_2$CH$_2$OH)$_2$ <br>—NCO | —(CH$_2$—CH$_2$—CH$_2$—O)$_x$H, <br>—N[CH$_2$—CH$_2$—O—C(=O)—CH=CH$_2$]$_2$, <br>or <br>—N[CH$_2$—CH$_2$—NH—C(=O)—CH=CH$_2$]$_2$, <br>where x is an integer from 1 to 18. <br>—NH$_2$, <br>—N(CH$_3$)$_2$, <br>—O—C(=O)—CH=CH$_2$, <br>—NCO, <br>—O—C(=O)—(CH$_2$)$_x$—CH$_3$, <br>—NH—C(=O)CH=CH$_2$, <br>—O—Z, <br>—O—(CH$_2$)$_7$—CH$_3$, <br>—NH—Z, or <br>—N(CH$_2$—CH$_2$—OH)$_2$. <br>—OH, <br>—NH$_2$, <br>—O—Z, <br>—N(Z)$_2$, <br>—N(CH$_2$—O—Z)$_2$, <br>or <br>—N(CH$_2$OH)$_2$. <br>—N(Z)$_2$, <br>—N(CH$_2$CH$_2$—O—Z)$_2$, <br>—N(CH$_2$CH$_2$—NH$_2$)$_2$, <br>or <br>—O—C(=O)—CH—CH$_2$. <br>—N(CH$_2$CH$_2$—O—Z)$_2$, <br>—N(CH$_2$NH$_2$)$_2$, <br>—N(CH$_2$CH$_2$OH)$_2$, <br>—CH$_2$—O—Z, <br>—CH$_2$—OH, <br>—CH$_2$—NH$_2$, <br>—N(CH$_3$)$_2$, <br>—O-(alkylene)—CH$_3$, <br>or <br>—CH$_2$—Y. <br>—NCO, <br>—O—C(=O)—(CH$_2$)$_x$—CH$_3$, <br>—NH—Z, <br>—N[CH$_2$O—C(=O)—CH=CH$_2$]$_2$, <br>—NH—C(=O)CH=CH$_2$, <br>—CH$_2$CH$_2$—O—Z, <br>or <br>—CH$_2$CH$_2$OH. <br>—N(Z)$_2$, <br>—N(CH$_2$—O—Z)$_2$, <br>—N(CH$_2$—CH$_2$—NH$_2$)$_2$ <br>or <br>—O—C(=O)—CH=CH$_2$. <br>—O—C(=O)—CH=CH$_2$ <br>—N(CH$_3$)$_2$ <br>—O—Z <br>—NH$_2$ <br>—NCO <br>—O—C(=O)—(CH$_2$)$_6$—CH$_3$ <br>—NH—C(=O)CH=CH$_2$ <br>—O—(CH$_2$)$_7$—CH$_3$ <br>—NH—Z <br>—N(CH$_2$CH$_2$OH)$_2$ <br>—NCO |

Non-limiting examples of phenolic compounds represented by formula I include, but are not limited to, the following compounds:

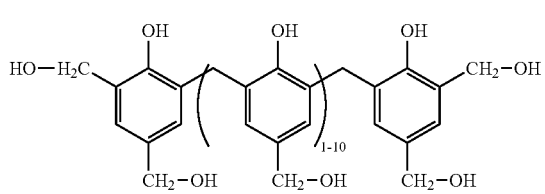

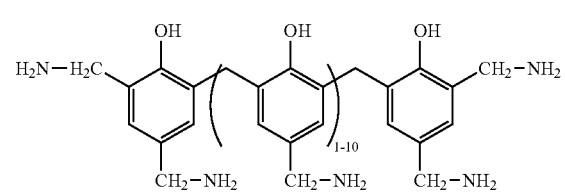

-continued
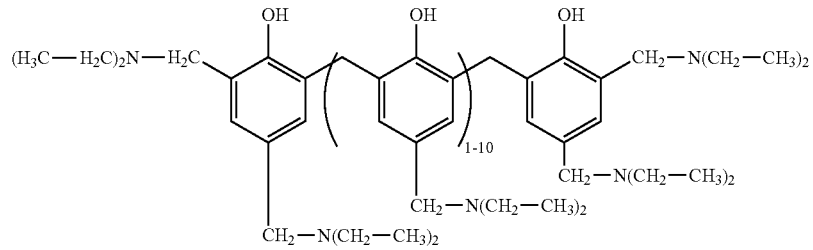
3
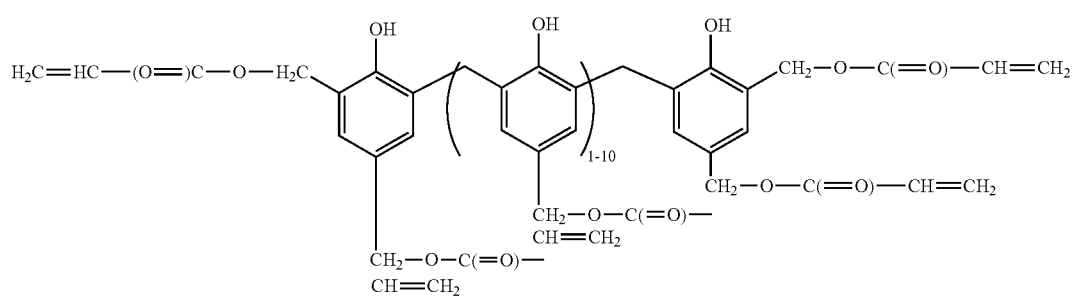
4
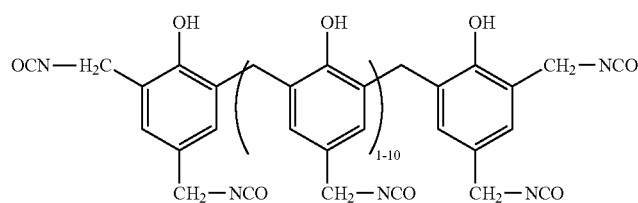
5
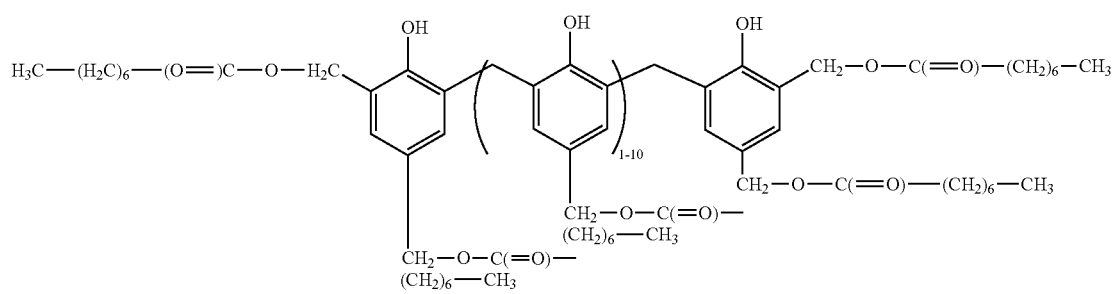
6
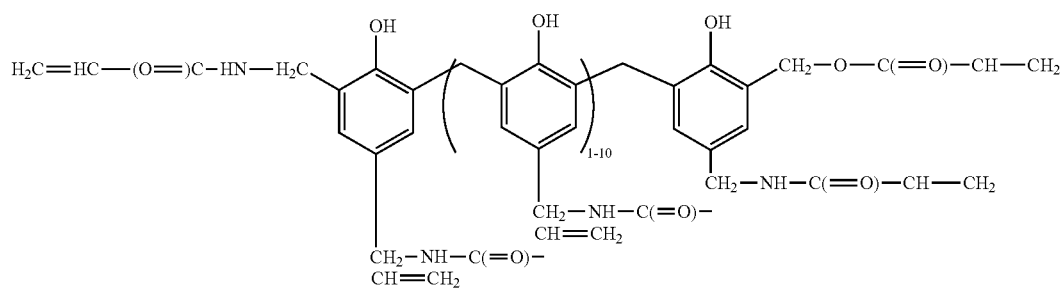
7

-continued

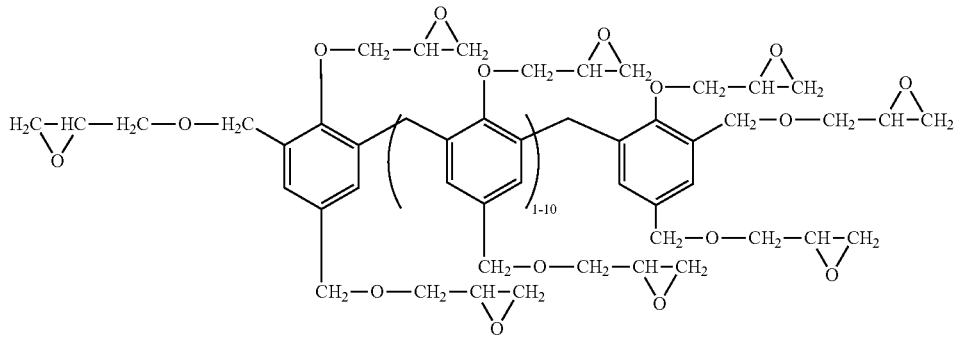
8

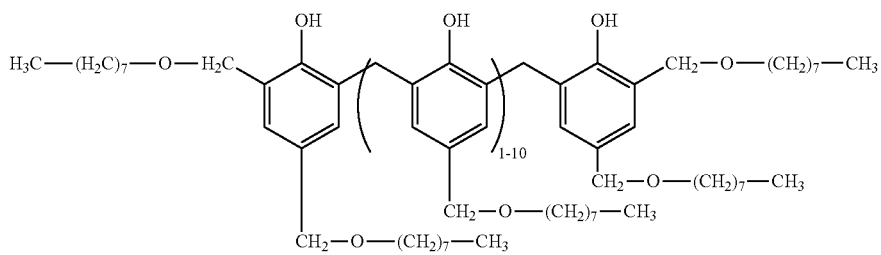
9

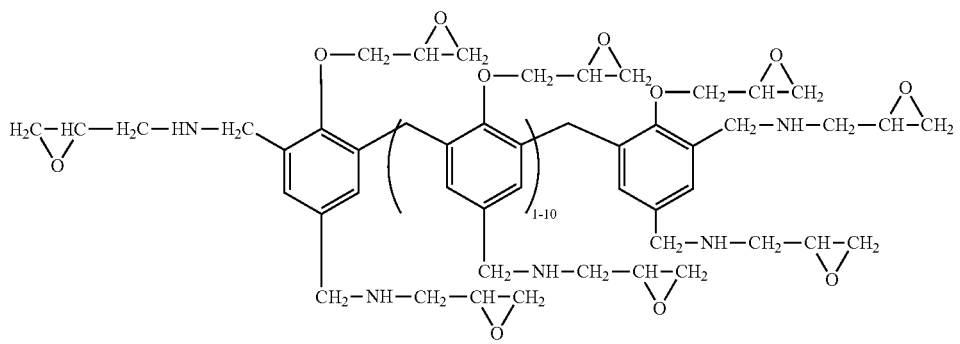
10

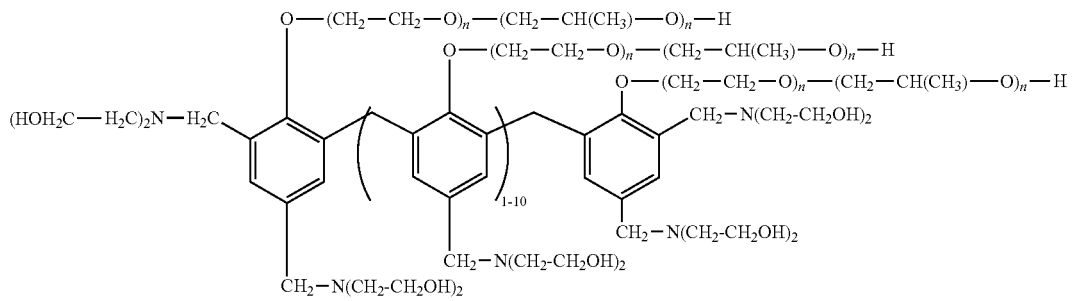
11

In some embodiments, methods for preparing compounds described herein may comprise: contacting a novolac compound with a formaldehyde or paraformaldehyde to form a hydroxymethyl compound; and contacting the hydroxymethyl compound with an epihalohydrin, an acrylic compound, an alkanoyl halide, an alkyl halide, ammonia, phosgene, or dialkylamine to form the compound. One example of such a reaction mechanism, outlined in FIG. 1, shows that novolac compound is reacted with formaldehyde to obtain compound 1. Compound 1 may be reacted with ammonia, diethylamine, acrylic anhydride, phosgene, isooctanoyl chloride, epichlorohydrin, or isooctyl chloride to obtain compounds 2, 3, 4, 5, 6, 8, and 9, respectively. Compound 2 may be reacted with any one of acrylic anhydride or epichlorohydrin to obtain compounds 7 and 10, respectively.

In some embodiments, contacting the phenolic compound with the formaldehyde or paraformaldehyde is performed in the presence of a basic catalyst. Examples of basic catalysts include, but are not limited to, alkali metal hydroxides, such as KOH, LiOH, NaOH, and the like. The phenolic compound and the formaldehyde or paraformaldehyde may be reacted in a molar ratio from about 1:3 to about 1:10, about 1:3 to about 1:8, about 1:3 to about 1:5, or about 1:3 to about 1:4. Examples also include about 1:10, about 1:8, about 1:6, about 1:4, about 1:3, and ranges between any two of these values (including their endpoints). During the reaction of the phenolic compound and the formaldehyde or paraformaldehyde, the pH of the solution may be maintained between about pH 8 to about pH 11, about pH 8 to about pH 10, about pH 8 to about pH 9, or about pH 8 to about pH 8.5. Examples also include about pH 8, about pH 8.5, about pH 9, about pH 10, about pH 11, and ranges between any two of these values (including their endpoints).

During the reaction of the phenolic compound and the formaldehyde or paraformaldehyde, the reaction mixture may be heated to an elevated temperature, such as a temperature of about 50° C. to about 70° C., about 50° C. to about 65° C., or about 50° C. to about 60° C. Examples also include temperatures of about 50° C., about 55° C., about 60° C., about 65° C., about 70° C., and ranges between (and including the endpoints of) any two of these values. The heating may be performed for a variety of times, such as about 2 hours to about 6 hours, for about 2 hours to about 5 hours, for about 2 hours to about 4 hours, or for about 2 hours to about 3 hours. Examples also include about 2 hours, about 3 hours, about 4 hours, about 5 hours, about 6 hours, and ranges between (an including the endpoints of) any two of these values. The reaction time may vary with the reaction temperature inversely. For example, if the reaction temperature is higher, the reaction time period may be shorter.

In some embodiments, novolac compounds with epoxy groups may be prepared by reacting a hydroxymethyl compound with an epihalohydrin compound in a molar ratio from about 1:3 to about 1:10, about 1:3 to about 1:7, about 1:3 to about 1:6, or about 1:3 to about 1:4. Examples also include about 1:3, about 1:4, about 1:6, about 1:8, about 1:10, and ranges between any two of these values (including their endpoints). The molar ratio of epihalohydrin to the hydroxymethyl compound may also depend on the number of hydroxyl groups present on the hydroxymethyl compound, and taking into consideration that one epichlorohyrin molecule may react with one hydroxyl group. In some embodiments, the epihalohydrin molecule may be used in molar excess of the hydroxyl groups. Examples of the epihalohydrin compound that may be used in the reaction include, but are not limited to, epichlorohydrin, epibromohydrin and methylepichlorohydrin. In some embodiments, the hydroxymethyl compound and the epihalohydrin compound may be heated to an elevated temperature, such as a temperature of about 50° C. to about 90° C., about 50° C. to about 75° C., about 50° C. to about 70° C., or about 50° C. to about 60° C. Examples also include about 50° C., about 65° C., about 70° C., about 80° C., about 85° C., about 90° C., and ranges between (and including the endpoints of) any two of these values. The heating may be performed for a variety of times, such as about 2 hours to about 6 hours, for about 2 hours to about 5 hours, for about 2 hours to about 4 hours, or for about 2 hours to about 3 hours. Examples also include about 2 hours, about 3 hours, about 4 hours, about 5 hours, about 6 hours, and ranges between (an including the endpoints of) any two of these values. In some embodiments, the reaction may involve a two-step heating process: heating the reaction mixture to a first lower temperature, and heating the reaction mixture to a second higher temperature to obtain a high degree of condensation of epihalohydrin and hydroxymethyl compound.

The reactions between the hydroxymethyl compound and the epihalohydrin compound may be performed in the presence of a reaction catalyst. Suitable reaction catalysts include, but are not limited to, $MgClO_4$, LiCl, LiOH, $SnF_2$, $LiClO_4$, or a combination thereof. In addition, the reaction rate may be increased by adding an organic solvent and performing the reaction in an emulsion system. Examples of organic solvents include, but are not limited to, 1-butanol, secondary butanols, glycol ethers such as 2-methoxyethanol, 2-ethoxyethanol, and 2-phenoxyethanol, ethers such as 1,4-dioxane, 1,3-dioxane and diethoxyethane, and aprotic polar solvents such as acetonitrile, dimethyl sulfoxide, and dimethyl formamide. These organic solvents may be used alone or in combination so as to adjust polarity.

For the purpose of, for example, improving the reaction rate, the reaction may be conducted in the presence of a phase transfer catalyst, such as, for example, quaternary ammonium salts. Examples include, but are not limited to, benzyltrimethylammonium bromide, cetyltrimethylammonium bromide, tetrabutylammonium hydroxide, tetrabutyl ammonium chloride and any combination thereof.

The reaction product obtained from the above methods described herein may be washed with, for example, water. Using the resulting product of the reaction between the hydroxymethyl compound and the epihalohydrin compound as an example, the unreacted epihalohydrin compound and the organic solvent may be distilled off by distillation with heating under reduced pressure. To obtain a compound containing a small amount of a hydrolysable halogen, the dehydrochlorination step may be performed under optimum conditions so that all the chlorohydrin derivatives are converted to epoxides. To remove the salt content, the resulting product may be dissolved in an organic solvent, such as toluene, methyl isobutyl ketone or methyl ethyl ketone, and the salt can be removed by filtration or by washing with water. The organic solvent may be distilled off by heating under reduced pressure to obtain a high-purity epoxy resin. An example compound prepared by this method is compound 7.

In some embodiments, novolac compounds with amino groups may be prepared by contacting the hydroxymethyl compound with ammonia in a molar ratio from about 1:3 to about 1:10, about 1:3 to about 1:8, about 1:3 to about 1:6, or about 1:3 to about 1:4. Examples also include about 1:3, about 1:5, about 1:7, about 1:8, about 1:10, and ranges between any two of these values (including their endpoints). The hydroxymethyl compound and the ammonia may be heated to an elevated temperature, such as a temperature of about 50° C. to about 70° C., about 50° C. to about 65° C., about 50° C. to about 60° C., or about 50° C. to about 55° C. Examples also include about 50° C., about 55° C., about 65° C., about 70° C., and ranges between (and including the endpoints of) any two of these values. In some embodiments, the hydroxymethyl compound and the ammonia may be heated under an elevated pressure, such as a pressure of about 1 atmosphere to about 1.5 atmospheres, about 1 atmosphere to about 1.35 atmospheres, or about 1 atmosphere to about 1.15 atmospheres. Examples also include about 1 atmosphere, about 1.15 atmospheres, about 1.25 atmospheres, about 1.35 atmospheres, about 1.5 atmospheres, and ranges between (and including the endpoints of) any two of these values. One example of such a compound prepared by this method is compound 2. In some embodiments, a novolac compound with primary amine, secondary amine, quaternary ammonium salts, or polyamine groups may be prepared by the methods described herein.

In some embodiments, novolac compounds with acrylate functional groups may be prepared by contacting a hydroxymethyl compound with an acrylic compound in a molar ratio from about 1:3 to about 1:10, from about 1:3 about 1:7, from about 1:3 to about 1:6, or from about 1:3 to about 1:5. Examples also include, but are not limited to, about 1:3, about 1:5, about 1:7, about 1:9, about 1:10, and ranges between any two of these values (including their endpoints). The acrylic compound may be acrylic anhydride, acryloyl chloride, acrylic acid, or any combination thereof. In some embodiments, the contacting step may be carried out in the presence or absence of an antioxidant, such as tert-butylhydroquinone, substituted quinones, butylated hydroxyl toluene, or any combination thereof.

In some embodiments, the reaction of hydroxymethyl compound and the acrylic compound may be brought to about completion by heating the reaction mixture to an elevated temperature, such as a temperature of about 25° C. to about 90° C., of about 25° C. to about 75° C., of about 25° C. to about 70° C., of about 25° C. to about 60° C., or of about 25° C. to about 40° C. Examples also include, but are not limited to, about 25° C., about 50° C., about 65° C., about 70° C., about 80° C., about 85° C., about 90° C., and ranges between (and including the endpoints of) any two of these values. The heating may be performed for a variety of times, such as about 2 hours to about 6 hours, for about 2 hours to about 5 hours, for about 2 hours to about 4 hours, or for about 2 hours to about 3 hours. Examples also include, but are not limited to, about 2 hours, about 3 hours, about 4 hours, about 5 hours, about 6 hours, and ranges between (and including the endpoints of) any two of these values. An example of such a compound prepared by this method is compound 4. In addition, the phenolic hydroxyl groups of compound 4 can be acrylated or epoxidized to produce acrylate epoxy alloys or reacted with ethoxylated ethers to produce hydrophilic acrylate emulsions for self-cleaning smart hydrophilic paints.

In some embodiments, novolac compounds with dialkylamino groups may be prepared by contacting a hydroxymethyl compound with a dialkylamine in a molar ratio from about 1:3 to about 1:10, about 1:3 to about 1:7, about 1:3 to about 1:6, or about 1:3 to about 1:5. Examples also include about 1:3, about 1:4, about 1:6, about 1:8, about 1:10, and ranges between any two of these values (including their endpoints). The molar ratio of dialkylamine to the hydroxymethyl compound may also depend on the number of the hydroxyl groups present on the hydroxymethyl compound, and taking into consideration that one dialkylamine molecule may react with one hydroxyl group. In some embodiments, the dialkylamine molecule may be used in molar excess of the hydroxyl groups. Non-limiting examples of dialkyl amine include dimethyl amine, diethyl amine, dipropyl amine, dibutyl amine, or any combination thereof. In some embodiments, the hydroxymethyl compound and the dialkylamine may be heated to a temperature of about 50° C. to about 70° C., about 50° C. to about 65° C., about 50° C. to about 60° C., or about 50° C. to about 55° C. Examples also include about 50° C., about 55° C., about 60° C., about 70° C., and ranges between (and including the endpoints of) any two of these values. The heating may be performed for about 2 hours to about 6 hours, for about 2 hours to about 5 hours, for about 2 hours to about 4 hours, or for about 2 hours to about 3 hours. Examples also include about 2 hours, about 3 hours, about 4 hours, about 5 hours, about 6 hours, and ranges between (an including the endpoints of) any two of these values.

The reactions between hydroxymethyl compounds and dialkyl amine compounds may be performed in the presence of a reaction catalyst. Suitable reaction catalysts include, but are not limited to, $MgClO_4$, $LiCl$, $LiOH$, $SnF_2$, $LiClO_4$, or a combination thereof. In addition, the reaction rate may be increased by adding an organic solvent and performing the reaction in an emulsion system. Examples of organic solvents include, but are not limited to, acetone, methyl ethyl ketone, methanol, tetrahydrofuran, 1,4-dioxane, 1,3-dioxane, diethoxyethane, dimethyl sulfoxide, dimethyl formamide, and combinations thereof. An examplary compound prepared by this method is compound 3. Dialkylamino novolac compounds (compound 3) may have a wide range of applications, such as an activator, a hardener for epoxy resins, a potential catalyst for polyurethane and silicon polymers, a cation exchange resin and as a septiciding agent.

In some embodiments, novolac compounds with alkanoate functional groups may be prepared by reacting a hydroxymethyl compound and analkanoyl halide in a molar ratio from about 1:3 to about 1:10, about 1:3 to about 1:7, about 1:3 to about 1:6, or about 1:3 to about 1:5. Examples also include about 1:3, about 1:4, about 1:6, about 1:8, about 1:10, and ranges between any two of these values (including their endpoints). Non-limiting examples of alkanoyl halide include isooctanoyl chloride, decanoyl chloride, hexanoyl chloride, lauroyl chloride, nonanoyl chloride, palmitoyl chloride, or any combination thereof. In some embodiments, the hydroxymethyl compound and the dialkylamine may be heated to a temperature of about 50° C. to about 90° C., about 50° C. to about 85° C., about 50° C. to about 70° C., or about 50° C. to about 55° C. Examples also include about 50° C., about 65° C., about 70° C., about 80° C., about 90° C., and ranges between (and including the endpoints of) any two of these values. The heating may be performed for about 2 hours to about 6 hours, for about 2 hours to about 5 hours, for about 2 hours to about 4 hours, or for about 2 hours to about 3 hours. Examples also include about 2 hours, about 3 hours, about 4 hours, about 5 hours, about 6 hours, and ranges between (and including the endpoints of) any two of these values. An examplary compound prepared by this method is compound 6. Compound 6 may have a wide range of applications, such as a plasticizer, an anti-oxidant, or a vibration damping resin.

In some embodiments, novolac compounds with alkyl ether groups may be prepared by contacting a hydroxymethyl compound and an alkyl halide in a molar ratio from about 1:3 to about 1:10, about 1:3 to about 1:7, about 1:3 to about 1:6, or about 1:3 to about 1:5. Examples include about 1:3, about 1:4, about 1:6, about 1:8, about 1:10, and ranges between any two of these values (including their endpoints). Non-limiting examples of alkyl halide include isooctyl chloride, decyl chloride, hexyl chloride, heptyl chloride, nonyl chloride, or any combination thereof. In some embodiments, the hydroxymethyl compound and the dialkylamine may be heated to a temperature of about 50° C. to about 90° C., about 50° C. to about 85° C., about 50° C. to about 70° C., or about 50° C. to about 55° C. Examples also include about 50° C., about 65° C., about 70° C., about 80° C., about 90° C., and ranges between (and including the endpoints of) any two of these values. The heating may be performed for about 2 hours to about 6 hours, for about 2 hours to about 5 hours, for about 2 hours to about 4 hours, or for about 2 hours to about 3 hours. Examples also include about 2 hours, about 3 hours, about 4 hours, about 5 hours, about 6 hours, and ranges between (an including the endpoints of) any two of these values. An examplary compound prepared by this method is compound 9. Compound 9 may have a wide range of applications, such as plasticizers, anti-oxidants, or vibration damping resins.

In some embodiments, novolac compounds with isocyanate functional groups may be prepared by contacting a hydroxymethyl compound and phosgene in a molar ratio from about 1:3 to about 1:10, about 1:3 to about 1:8, about 1:3 to about 1:6, or about 1:3 to about 1:4. Examples include about 1:3, about 1:5, about 1:7, about 1:8, about 1:10, and ranges between any two of these values (including their endpoints). The hydroxymethyl compound and the phosgene may be heated to a temperature of about 50° C. to about 70° C., about 50° C. to about 65° C., about 50° C. to about 60° C., or about 50° C. to about 55° C. Examples also include about 50° C., about 55° C., about 65° C., about 70° C., and ranges between (and including the endpoints of) any two of these values. In some embodiments, the hydroxymethyl compound and the phosgene may be heated under a pressure of about 1 atmosphere to about 1.5 atmospheres, about 1 atmosphere to about 1.35 atmospheres, or about 1 atmosphere to about 1.15 atmospheres. Examples include about 1 atmosphere, about 1.15 atmospheres, about 1.25 atmospheres, about 1.35 atmospheres, about 1.5 atmospheres, and ranges between (and including the endpoints of) any two of these values. In some embodiments, $CO_2$ may be substituted for phosgene. In some embodiments, the phenolic —OH groups on compound 5 can be pre-reacted to form epoxy glycidyl ether or acrylate as a new source for polymeric alloys (acrylate-urethane, epoxy-urethane or epoxy-acrylate urethane) or polyethyleneoxide. An examplary compound prepared by this method is compound 5. Compound 5 can also be used as a blocking agent to protect isocyanate groups in water-based applications.

Compounds of the present disclosure may be used as, for example, thermosets, electrical insulators for high-voltage generators, curing agents for manufacturing brake pads, hydrogels, hydrogel surfactants, binding resins for ablative thermal insulators, ceramics, catalysts, hardeners, surfactants, vibration damping agents, plasticizers, anti-oxidants, insecticides, crosslinking agents, or any combinations thereof. These compounds may enhance the thermal stability, glass transition temperature and/or the chemical resistance of the resins due to the aromatic structures and multi-functionality. Examples of such resins in which the compounds may be incorporated include, but are not limited to, polyurethanes, silicones, commercial epoxy resins, urea-formaldehyde resins, melamine-formaldehyde resins, hydroxymethyl urea-formaldehyde resins, hydroxymethyl melamine-formaldehyde resins and the like.

In addition, compounds of the present disclosure may be cured to form resins. A variety of curing agents may be used for this process. Curing agents include acid catalysts, peroxides, or any commercially available hardeners. In some embodiments, compounds described herein may themselves be used as curing agents. For example, compound 2 may be used as a curing agent for epoxy resin derivatives.

Resins manufactured from the compounds of the present disclosure may be blended with, for example, other materials such as solvents or diluents, fillers, pigments, dyes, flow modifiers, thickeners, reinforcing agents, mold release agents, wetting agents, stabilizers, fire retardant agents, surfactants and combinations thereof. These additives may be added in functionally equivalent amounts to obtain the desired properties.

The poly-functional epoxy and amine resins prepared according to the disclosure may have a high glass transition temperature and may display high thermal stability. Resins with such properties may be well suited for use as, for example, binders for composite materials. Further, the multi-functional epoxy resins may have a higher degree of cross-linking resulting in improved resistance to solvents and/or corrosive chemicals. The resins made from the compounds of the present disclosure may have improved water miscibility when compared to the common aromatic epoxy resins, and accordingly such a resin may be used for applications in, for example, in a humid environment, on a wet surface, as a water-based epoxy for construction work and as a water-based paint.

The resins of the present disclosure may be employed in, for example, encapsulations, electronic or structural laminates or composites, filament winding, molding, semiconductor encapsulating materials, under-fill materials, conductive pastes, laminates, resin compositions used for electronic circuit boards, resin casting materials, adhesives, interlayer insulation materials for buildup substrates, and coating materials, such as insulating paint. Further, these resins may also be used as linings in articles of manufacture including, but not limited to, tanks, cars, drums, pails, pipes, down-hole oilfield tubings, and food cans. In addition, the resins may be used as, for example, laminated epoxy structures for concrete molds, honeycomb cores, wood and metal assemblies, and reinforced pipes.

Epoxy resins of the present disclosure may be used with, for example, acrylic systems to provide excellent coatings for articles of manufacture, such as appliances, kitchen cabinets, outdoor furniture, aluminum siding, and other metal products. The poly-functional epoxy and amine resins may be used as, for example, a powder coating for anti-corrosion or a high sheen decorative coating. Such coatings may find applications in articles of manufacture such as, washing machines, appliances, ships, bridges, pipelines, chemical plants, automobiles, farm implements, containers, and floor surfaces.

The phenolic compounds with acrylate functional groups may be used, for example, as binders in paints and coatings. In addition, various additives, such as pigments, coalescing agents, rheology modifiers, fungicides, plasticizers, nitrates, and the like, may be added to the coatings. Paints with multi-functional acrylate binders may display high glass transition temperatures, and may be resistant to abrasion, and easily cure at room temperature. The coatings may generally be applied to any substrate. The substrate may be, for example, an article, an object, a vehicle or a structure. Although no particular limitation is imposed on the substrate to be used in the present disclosure, examples of such substrates include, building exteriors, vehicles, bridges, airplanes, metal railings, fences, glasses, plastics, metals, ceramics, wood, stones, cement, fabric, paper, leather, and combinations or laminations thereof may be used. The coating may be applied to a substrate by, for example, spraying, dipping, rolling, brushing, or any combination thereof.

The resins formed from the acrylate compounds described herein may be used for production of composites, either alone or as interpenetrating polymer networks (IPNs) with other thermosets, such as epoxy and unsaturated polyesters. Further, these resins may also find use in, for example, hydrogels, polyacrylate super absorbent polymers (SAPs), adhesives, composites, sealants, fillers, fire retardants, cross-linking agents, and the like. In addition, resins may be prepared with different functionality such that a different number of acrylate functional groups per monomer are exhibited. For example, by using a resol precursor a resin with 4 acrylate groups per monomer may be prepared. In contrast, a melamine precursor may result in 6 acrylate groups per monomer. Such resins with tailored functionality may be used to improve the physical, mechanical and/or chemical properties, and curing characteristics of acrylate emulsions. The resins described herein may be used as a crosslinking agent for commercial acrylate resins, and/or as a wetting polymeric surfactant, and such properties may find applications in super absorbent polymers for soil treatment.

The compounds of the present disclosure may also be used as a precursor for developing new and improved products for hydrophobic soil treatment, or for use in water and sewage treatment facilities with compounds that act as water-clarification agents. Further, compounds described herein may find use in carbon fibers, crosslinking agents for SAPs, adhesives, lamination, photo printing, room-temperature curing applications, photo curing, and the like.

EXAMPLES

Example 1: Preparation of Hydroxymethyl Compound-Resolac (Compound 1)

Figure 2A:
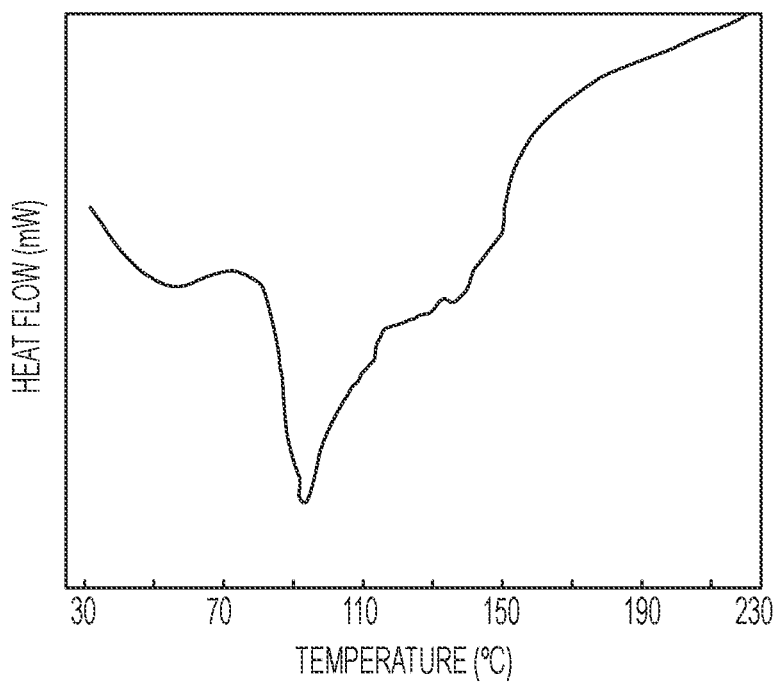
FIG. 2A depicts a DSC thermogram of compound 1 measured at 10° C./minute under N$_2$ atmosphere according to an embodiment.
Figure 2B:
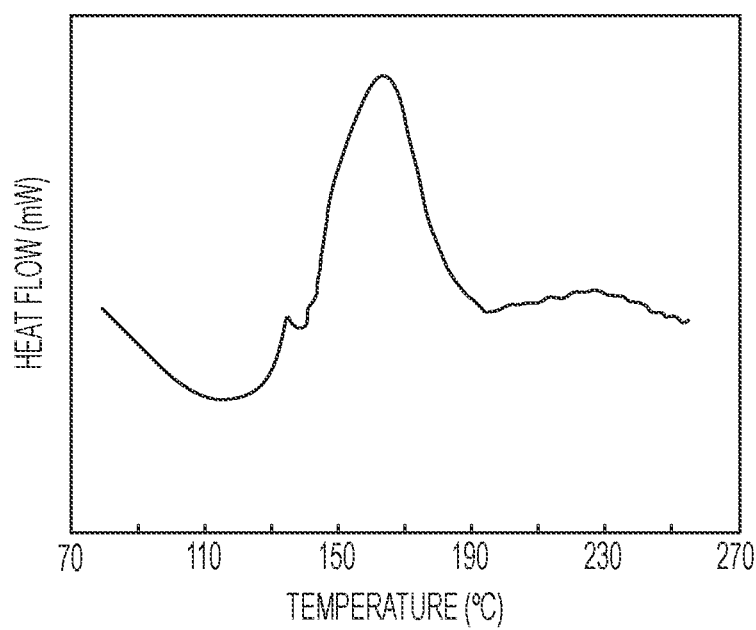
FIG. 2B shows a DSC thermogram of novolac cured with hexamine according to an embodiment.
Figure 3:
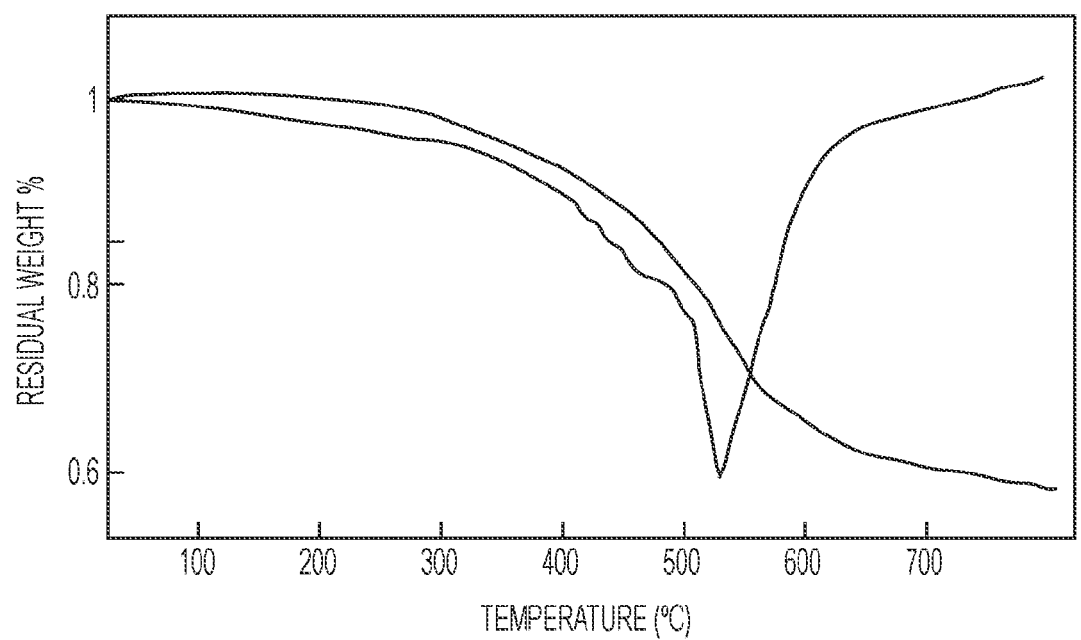
FIG. 3 depicts the TGA curves of compound 1 according to an embodiment.

About 150 grams of low molecular weight novolac and 200 grams of formalin solution (37% by weight) were mixed in a five-neck reaction flask fitted with a condenser, a mechanical stirrer, dropping funnel, and a thermometer. The reaction was started by adding 150 mL of 10% (by weight) sodium hydroxide solution drop wise, and the pH of the reaction mixture was adjusted between pH 9-10. The reaction mixture was heated to about 65° C. for 3 hours. At the end of this period, the reaction mixture was cooled and neutralized with a cold (5-10° C.) solution of sodium dihydrogen phosphate. A golden colored resin layer was separated from the reaction mixture, dissolved in ethanol, desalted, and dried with molecular sieves. The product was evaporated by rotary evaporators and dried under vacuum to obtain compound 1. The product was characterized and its curing properties were investigated by differential scanning calorimetry (DSC). A typical DSC thermogram for compound 1 measured at a constant rate of change in temperature (10° C./minute under $N_2$ atmosphere) is shown in FIG. 2A. For comparison, a DSC thermogram of novolac cured with hexamine is shown in FIG. 2B. A representative thermogravimetric analysis (TGA) of compound 1 is shown in FIG. 3.

Example 2: Preparation of Amino Novolac Compound (Compound 2)

About 30.6 grams of compound 1 was mixed with 150 mL of ethanol in a one liter autoclave system from Analis (Belgium) that is fitted with a mechanical stirrer, and which could be operated under controlled temperature and pressure. The system was secured and connected to an ammonia gas cylinder. The system was flushed with $N_2$, and mixed for 10 minutes to dissolve the compound. Ammonia gas was fed to the autoclave until the pressure reached 1.5 atmospheres. The reaction temperature was maintained at 50-70° C. via the cooling jacket of the autoclave for 2 hours. At the end of this period, the system was cooled to room temperature and the system was flushed with $N_2$ gas to remove unreacted ammonia gas. The white milky syrup product was evaporated and dried under vacuum to obtain compound 2. The number of amino groups present, based on the percent N content, was determined by CHN microanalysis. The CHN data showed that the number of amino groups (based on percent N content) were 10 and 5, for novolacs of molecular weight 700 and 1000, respectively. The purified resin was used as a hardening agent for epoxies, and as a catalyst and crosslinking agent for polyurethanes and siloxanes.

Example 3: Preparation of Diethylamino Derivative (Compound 3)

About 45 grams of compound 1 was refluxed with 300 grams of diethylamine (DEA) for three hours. At the end of this period, the product was cooled to room temperature, and the unreacted DEA was extracted with water several times. The obtained oily resin was dissolved in ethanol and dried with molecular sieves. The product was evaporated by rotary evaporator and dried under vacuum at 80° C. and 0.1 mm Hg for 3 hours to obtain compound 3. The number of diethylamine groups was determined from CHN microanalysis. The number of substituted aminogroups was less than the number of hydroxymethyl groups by 20-30%, due to the catalytic polymerization of resolac in the presence of DEA. The number of estimated DEA groups was about 5-7 groups per resolac molecule.

Example 4: Preparation of Acrylate Compound (Compound 4)

Figure 4:
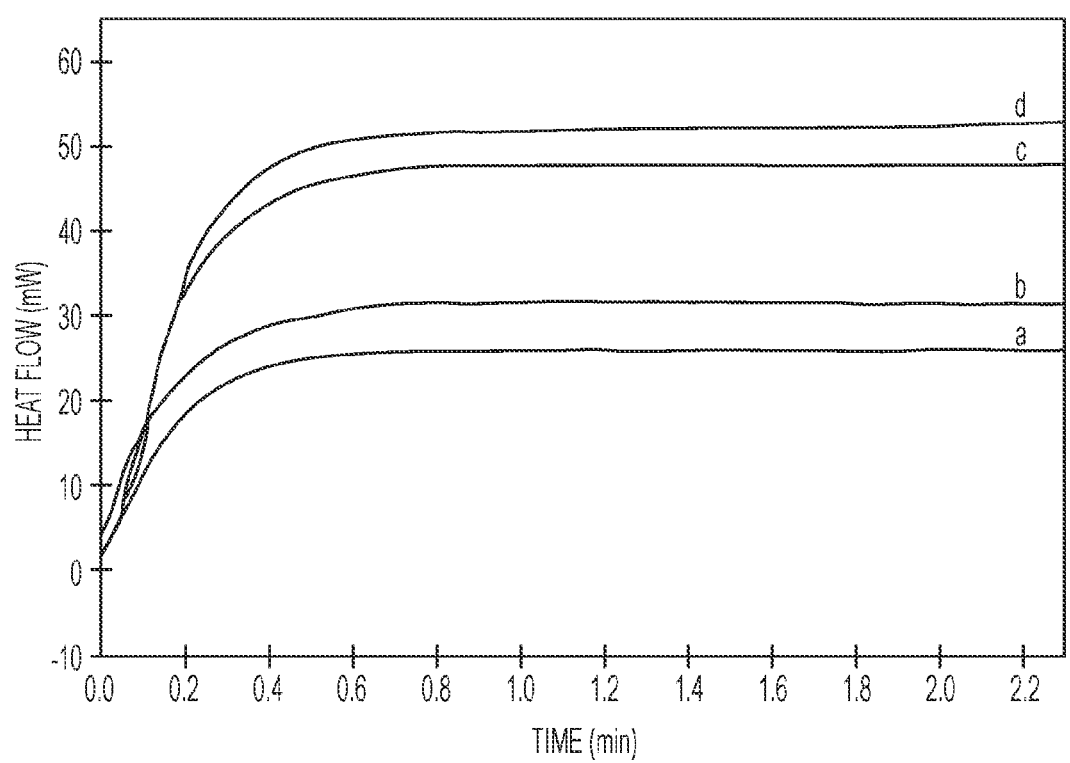
FIG. 4 depicts the isothermal DSC curing curves of compound 4 at temperatures 40° C., 50° C., 60° C. and 80° C., according to an embodiment.

About 22 grams of compound 1 was diluted with 10% THF and mixed with 86 grams (0.4 mole) of acrylic anhydride (analar grade) and 0.1 gram of tert-butylhydroquinone in a reaction vessel. The reaction mixture was heated to about 60° C. The reaction was continued at about 60° C. for two hours, and at the end of this period the temperature was raised to about 80° C. and heated for one more hour. Excess unreacted acrylic anhydride and acrylic acid by-products were distilled under vacuum, and a pale yellow viscous acrylated compound (compound 4) was obtained. The product was characterized and evaluated by DSC. The isothermal DSC curing curves for compound 4 at 40° C. (a), 50° C. (b), 60° C. (c), and 80° C. (d) are shown in FIG. 4. The measured glass transition temperature of compound 4 was 144° C.

The above product can also be prepared by substituting acrylic acid with acryloyl chloride and carrying out the reaction in the presence of triethylamine as HCl acceptor at ambient temperature (25° C.).

Example 5: Preparation of Polyisocyanate Compound (Compound 5)

About 45 grams of compound 1 dissolved in 150 mL of dry methylene chloride and about 20 grams of triethylamine as HCl acceptor are placed in 500 mL autoclave, as used in Example 2. The autoclave is secured and flushed with nitrogen. Phosgene is fed to the solution, and the reaction is continued under phosgene atmosphere for two hours. At the end of the reaction period, the system is flushed again with nitrogen, and unreacted phosgene is bubbled through a saturated solution of alcoholic potassium hydroxide. The product is separated to obtain compound 5. The isocyanate equivalent is determined by titration adopting standard methods and will be about 30-40% by weight.

Example 6: Preparation of Isooctonoate Compound (Compound 6)

A 500 mL three-neck reaction vessel fitted with a condenser, a dropping funnel, and a mechanical stirrer was immersed in a water bath. The dropping funnel was charged with about 22 grams of compound 1 diluted with 20 grams of triethylamine as a HCl acid acceptor. The reaction vessel was charged with about 30 grams of isooctanoyl chloride, and the reaction vessel was heated to 60° C. Compound 1 was added from the dropping funnel drop wise with efficient mixing over one hour. The reaction was continued at 60° C. for two hours. Later, the temperature was raised to 80° C. and the reaction was continued for one more hour. Excess unreacted isooctanoyl chloride and its amine adduct were separated. A yellow viscous resolac isooctanoate compound (compound 6) was obtained. The compound was characterized by IR, CHN, and cryoscopic molecular weight determination apparatus. The obtained molecular weight of the compound was between 3500-4200.

Example 7: Preparation of Acrylamide Compound (Compound 7)

Figure 5:
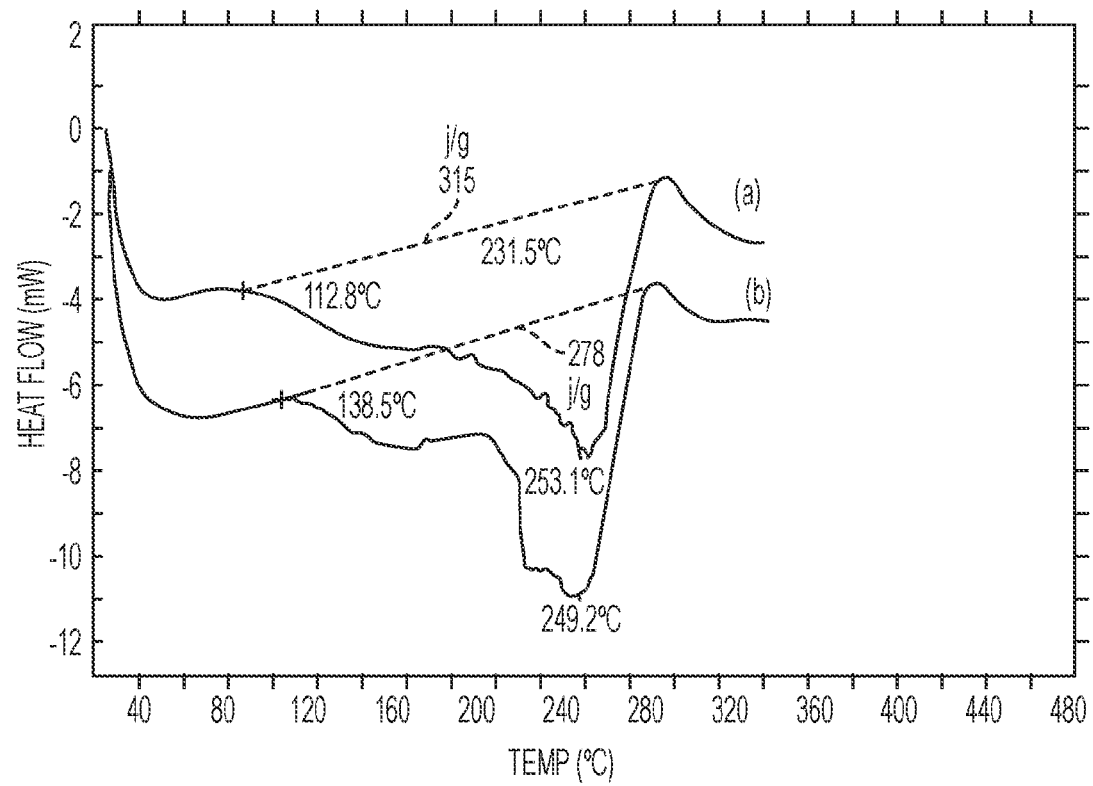
FIG. 5 depicts DSC curing curves of compound 7 at temperatures 40° C. and 60° C., according to an embodiment.

The reaction set up of Example 6 was used. The dropping funnel was charged with about 45 grams of compound 2 diluted with 10% THF. The reaction vessel was charged with 0.2 mole (44 grams) of acrylic anhydride and 0.2 grams of butylated hydroquinone. The reaction mixture was heated to 80° C., with slow addition of compound 2 for one hour. After the addition of the compound, the reaction was continued for further one hour. Excess unreacted acrylic anhydride and acrylic acid by-products were distilled under vacuum, and a pale yellow viscous acrylated compound (compound 7) was obtained. The product was characterized and evaluated by DSC. The compound is further polymerized to form a hydrogel wetting surfactant by modifying the phenolic groups to phenoxypoly ether, which is suitable for the treatment of hydrophobic soils. The above product can also be prepared by substituting acrylic anhydride with acryloyl chloride and carrying out the reaction in the presence of triethylamine as HCl acceptor at ambient temperature (25° C.). A representative DSC thermogram showing the curing of compound 7 (at 40° C. (a) and at 60° C. (b), measured at 10° C./minute), is shown in FIG. 5.

Example 8: Preparation of Epoxy Compound (Compound 8)

About 100 grams (0.2 mol) of compound 1 was combined with 1 gram of $MgClO_4$ dissolved in 5 mL of 2-methoxy ethanol, and 231 grams (2.5 mol) of epichlorohydrin. The system was flashed with nitrogen for 10 minutes with continuous mixing. The reaction temperature was raised to 60° C., and the reaction was continued for two hours. At the end of this period, the temperature was raised to 80-85° C., and the reaction was continued for 1 more hour. Later, the reaction mixture was cooled to 60° C., and about 12 grams of tetrabutyl ammonium chloride dissolved in 25 mL of water was added with continuous mixing, followed by addition of 250 ml of 50% (by weight) NaOH solution. The reaction mixture was stirred for 1 hour, and the mixture of epichlorohydrin and water was separated by azeotropic distillation. Separated epichlorohydrin was again introduced back into the reaction mixture, and the mixture was further heated to 70° C. for 60 minutes. The excess of unreacted epichlorohydrin was distilled under vacuum, and the reaction mixture was cooled to room temperature. The epoxy product formed was dissolved in toluene, filtered, washed with 1% (by weight) acetic acid, washed with water and dried with molecular sieves. The product was evaporated by rotary evaporators and dried under vacuum at 0.1 millimeter Hg at 40° C. for 6 hours to obtain a brownish colored viscous compound 8. The epoxy equivalent of the compound was determined adopting standard methods. The epoxy equivalent was found to be 86 grams/equivalent (epoxy equivalent=4.8 eq/kilogram), viscosity at 40° C. was 315.4 Pa·s, and active chlorine content was 1.3% by weight.

Example 9: Preparation of Isooctyl Ether Compound (Compound 9)

About 20 grams of resolac compound 1 is dissolved in tetrahydrofuran and modified to a sodium ether adduct by treating with sodium wire. Under dry conditions, the sodium resolac oxide derivative is reacted with isooctyl chloride, and the reaction is continued for two hours with efficient mixing. The oily yellow color ether plasticizer obtained is separated, washed with ethanol to decompose the unreacted sodium. The product is washed with water, and dried with molecular sieves to obtain compound 9. The product is evaluated for plasticizer and vibration damping agent properties.

Example 10: Preparation of Glycidylamine Compound (Compound 10)

About 45 grams of compound 2 is dissolved in 100 mL of DMF and combined with 1 gram of $MgClO_4$ dissolved in 5 mL of 2-methoxy ethanol, and 231 grams (2.5 mol) of epichlorohydrin. The system is flashed with nitrogen for 10 minutes with continuous mixing. The reaction temperature is raised to 60° C., and the reaction is continued for two hours. At the end of this period, the temperature is further raised to 80-85° C., and the reaction is continued for 1 more hour. Later, the reaction mixture is cooled to 60° C., and about 12 grams of tetrabutyl ammonium chloride dissolved in 25 mL water is added with continuous mixing, followed by addition of 250 ml of 50% (by weight) NaOH solution. The reaction mixture is stirred for 1 hour, and the mixture of epichlorohydrin and water is separated by azeotropic distillation. Separated epichlorohydrin is again introduced back into the reaction mixture, and the mixture is further heated to 70° C. for 60 minutes. The excess of unreacted epichlorohydrin is distilled under vacuum, and the reaction mixture is cooled to room temperature. The epoxy product formed is dissolved in toluene, filtered, washed with 1% (by weight) acetic acid, washed with water and dried with molecular sieves. The product is evaporated by rotary evaporators and dried under vacuum at 0.1 millimeter Hg at 40° C. for 6 hours to obtain a brownish colored viscous compound 10. The epoxy equivalent of the compound is determined adopting standard methods and will be 4-5 epoxy equivalent per kilogram of the compound.

Example 11: Use of Compound 1 as a Binder

A composition comprising 90% by weight fine silica sand (80-200 microns in diameter), 2.5% by weight rock wool, 2.5% by weight waste paper, and 5% by weight compound 1 was dissolved in 10% (v/v) ethanol. The composition was mixed until a homogenous product was obtained. The product was placed in a mold to form various shapes, such as a plate of dimension 80×80×5 centimeters, nozzles, and other refractory products. The cast products were cured in an oven at 80-100° C. for 2 hours. The products were removed from the mold and used in refractory applications.

Example 12: Use of Compound 1 and Compound 2 as a Binder

A composition comprising 90% by weight fine silica sand (80-200 microns in diameter), 2.5% by weight rock wool, 2.5% by weight waste paper, 2.5% by weight compound 2, and 2.5% by weight compound 1 was dissolved in 10% (v/v) ethanol. The composition was mixed until homogenous product was obtained. The product was placed in a mold to form various shapes, such as a plate of dimension 80×80×5 centimeters, nozzles, and other refractory products. The cast products were cured at room temperature overnight. The products were removed from the mold and used in refractory applications.

Example 13: Use of Compounds as an Electrical Insulators

A composition comprising compound 1 and compound 2 in a ratio of about 1:1 was prepared and diluted with 5%

(v/v) ethanol. The mixture was applied to electrical coils as insulators, and cured at room temperature. The mixture exhibited excellent electrical resistivity, and were resistant to high temperatures. These coils were used in electrical transformers.

Example 14: Evaluation of Resolac Plasticizers

Several compositions comprising a mixture of polyvinyl chloride (PVC), (5-10% by weight) compound 2 and (5-10% by weight) compound 6 was prepared. The rheological properties and thermal stability of the obtained compositions were measured by rheometer and melt flow rate. Compounds 2 and 6 showed remarkable efficiency in improving the melt flow rate of PVC when compared with commercial plasticizers, such as dioctylphthalate.

Example 15: An Article Coated with Epoxy Coating

A cast iron rod is coated with an epoxy paint prepared from compound 8. A similar rod is also coated with a commercially available non-epoxy paint. The paint is allowed to dry and scribed with an X through the paint down to the metal. The rods are placed in a salt fog chamber (5% by volume NaCl, 35° C.) for 200 hours. At the end of this period, the rods are visually inspected for corrosion and peeling of the paint at the site of damage. The rod sprayed with epoxy paint will display less corrosion and peeling of the paint, when compared to the rod sprayed with a non-epoxy paint.

Example 16: Preparation of a Hydrogel

About 10 grams of compound 7 was mixed with 2 grams of polyacrylate, 0.05 grams of benzoylperoxide and 0.02 grams of cobalt octanoate and left to cure at ambient temperature. The cured resin was later neutralized with potassium hydroxide. About 10 grams of the neutralized resin was immersed in distilled water. The product swelled in volume (about 200% increase in weight) due to absorption of water.

Figure 6:
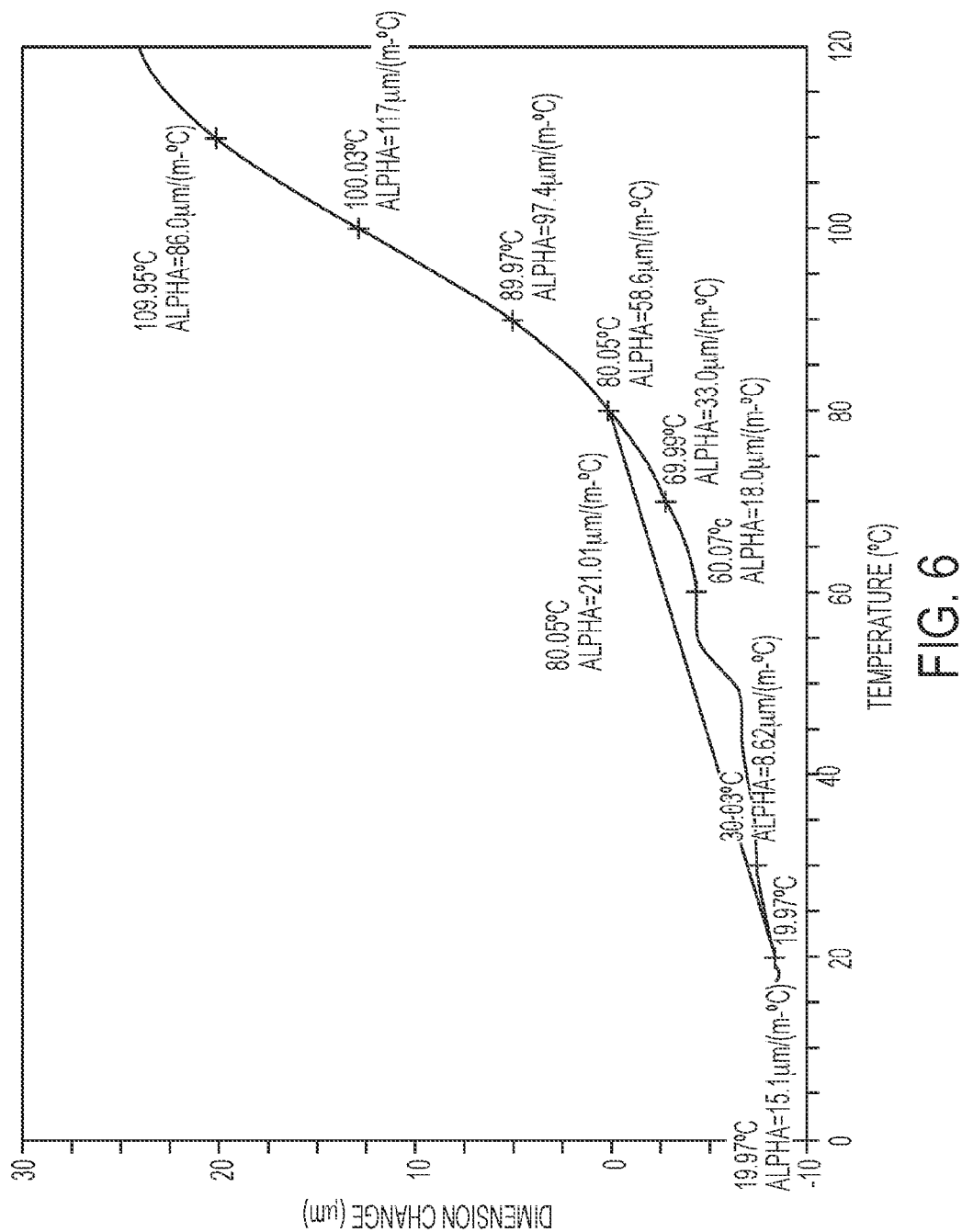
FIG. 6 depicts the thermomechanical curve showing high glass transition temperature and expansion coefficient of a cured epoxy resin according to an embodiment.

Example 17: Curing of an Epoxy Compound 10 grams of compound 8 was mixed with 3 grams of the commercial hardener 8050. The mixture was left to cure overnight to form a hard resin with a glass transition temperature of about 90° C. to about 100° C. The thermo-mechanical curve showing high glass transition temperature and expansion coefficient of the cured resin at various temperature ranges is depicted in FIG. 6.

Figure 7:
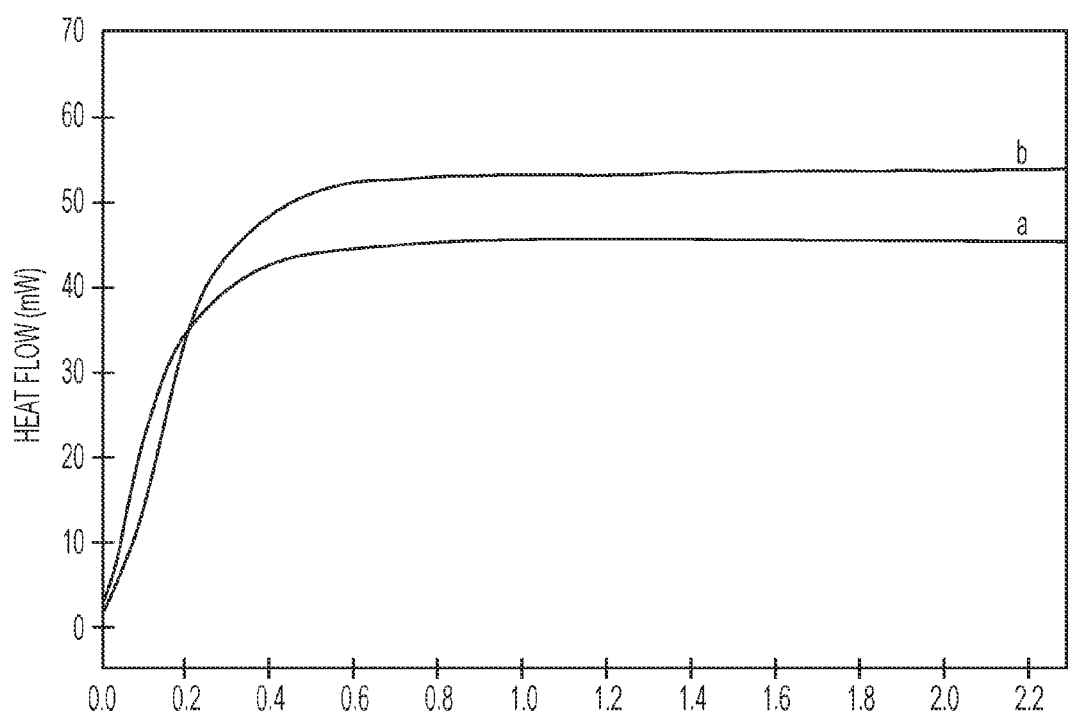
FIG. 7 represents DSC curing curves of acrylate resin at temperatures 40° C. and 60° C. according to an embodiment.

Example 18: Curing of Acrylate Resins 10 grams of acrylate compound 4 was mixed with 0.05 grams of benzoylperoxide and 0.02 grams of cobalt octanoate. The mixture was left to cure at ambient temperature for about 6 hours to about 12 hours. The cured polyacrylate resin had a glass transition temperature of 120-150° C. and a thermal decomposition temperature of 430° C. As will be appreciated, the acrylate resin can be easily cured at ambient temperature. The acrylate resin displays high glass transition and thermal decomposition temperatures. The DSC isothermal curing curves for acrylate resins at 40° C. and 60° C. are shown in FIG. 7.

Example 19: Manufacture of a Brake Pad

About 15 grams of resolac compound 1 is mixed with a filler composition made up of 10 grams of barium sulphate, 3.5 grams of asbestos, 1.5 grams of brass fillings, 5.5 grams of graphite powder, 5 grams of carbon fibers, 5 grams of ceramic microspheres, 2 grams of copper, 5 grams of fiberglass, 0.5 grams of calcium hydroxide, 12 grams of aluminum oxide, 0.2 grams of copper sulphide, 12 grams of quartz, 5 grams of rock wool, and 5 grams of recycled rubber scrap. The composition is mixed well and about 10 grams of compound 2 is added to this composition and remixed to get homogenous mixture. The mixture is pressed into a mold by a metal plate and then left to cure at room temperature for 6 hours. The product is further cured at 80° C. for 1 hour. A brake pad is obtained with good friction properties.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and one or more to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases one or more or "at" least one and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A compound of formula I:

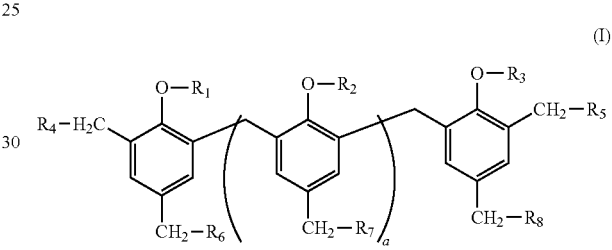

wherein:

a is an integer from 1 to 10;

$R_1$ is H, Z, —C(=O)—CH=CH$_2$, —(CH$_2$—CH$_2$—O)$_n$H, —(CH$_2$—CH$_2$—CH$_2$—O)$_n$H, or —(CH$_2$—CH$_2$—O)$_n$—(CH$_2$—CH(CH$_3$)—O)$_n$H, where each n is, independently, an integer from 1 to 18;

each $R_2$ is, independently, H, Z, —C(=O)—CH=CH$_2$, —(CH$_2$—CH$_2$—O)$_p$H, —(CH$_2$—CH$_2$—CH$_2$—O)$_p$H, or —(CH$_2$—CH$_2$—O)$_p$—(CH$_2$—CH(CH$_3$)—O)$_p$H, where each p is, independently, an integer from 1 to 18;

$R_3$ is H, Z, —C(=O)—CH=CH$_2$, —(CH$_2$—CH$_2$—O)$_q$H, —(CH$_2$—CH$_2$—CH$_2$—O)$_q$H, or —(CH$_2$—CH$_2$—O)$_q$—(CH$_2$—CH(CH$_3$)—O)$_q$H, where each q is, independently, an integer from 1 to 18;

$R_4$ is —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—(CH$_2$)$_r$—CH$_3$, —NH—Z, —N[CH$_2$O—C(=O)—CH=CH$_2$]$_2$, —NH—C(=O)CH=CH$_2$, —CH$_2$CH$_2$—O—Z, —CH$_2$CH$_2$OH, —O—C(=O)—CH=CH$_2$, —N(CH$_2$—CH$_2$—NH$_2$)$_2$, —(CH$_2$—CH$_2$—O)$_r$H, —(CH$_2$—CH$_2$—CH$_2$—O)$_r$H, —N[CH$_2$—CH$_2$—O—C(=O)—CH=CH$_2$]$_2$, or —N[CH$_2$—CH$_2$—NH—C(=O)—CH=CH$_2$]$_2$, where each r is, independently, an integer from 1 to 18;

$R_5$ is —OH, —NH$_2$, —O—Z, —N(Z)$_2$, —N(CH$_2$—O—Z)$_2$, —N(CH$_2$OH)$_2$, —N(CH$_2$CH$_2$—O—Z)$_2$, —N(CH$_2$NH$_2$)$_2$, —N(CH$_2$CH$_2$OH)$_2$, —CH$_2$—O—Z, —CH$_2$—OH, —CH$_2$—NH$_2$, —N(CH$_3$)$_2$, —O-(alkylene)-CH$_3$, —CH$_2$—Y, —NCO, —O—C(=O)—

$(CH_2)_t$—$CH_3$, —NH—Z, —N[$CH_2$—O—C(=O)—CH=$CH_2$]$_2$, —NH—C(=O)CH=$CH_2$, —$CH_2CH_2$—O—Z, —$CH_2CH_2$OH, —O—C(=O)—CH=$CH_2$, —N($CH_2$—$CH_2$—$NH_2$)$_2$, —($CH_2$—$CH_2$—O)$_t$H, —($CH_2$—$CH_2$—$CH_2$—O)$_t$H, —N[$CH_2$—$CH_2$—O—C(=O)—CH=$CH_2$]$_2$, or —N[$CH_2$—$CH_2$—NH—C(=O)—CH=$CH_2$]$_2$, where each t is, independently, an integer from 1 to 18;

$R_6$ is —OH, —$NH_2$, —O—Z, —N(Z)$_2$, —N($CH_2$—O—Z)$_2$, —N($CH_2$OH)$_2$, —N($CH_2CH_2$—O—Z)$_2$, —N($CH_2NH_2$)$_2$, —N($CH_2CH_2$OH)$_2$, —$CH_2$—O—Z, —$CH_2$—OH, —$CH_2$—$NH_2$, —N($CH_3$)$_2$, —O-(alkylene)-$CH_3$, —$CH_2$—Y, —NCO, —O—C(=O)—($CH_2$)$_v$—$CH_3$, —NH—Z, —N[$CH_2$O—C(=O)—CH=$CH_2$]$_2$, —NH—C(=O)CH=$CH_2$, —$CH_2CH_2$—O—Z, —$CH_2CH_2$OH, —O—C(=O)—CH=$CH_2$, —N($CH_2$—$CH_2$—$NH_2$)$_2$, —($CH_2$—$CH_2$—O)$_v$H, —($CH_2$—$CH_2$—$CH_2$—O)$_v$H, —N[$CH_2$—$CH_2$—O—C(=O)—CH=$CH_2$]$_2$, or —N[$CH_2$—$CH_2$—NH—C(=O)—CH=$CH_2$]$_2$, where each v is, independently, an integer from 1 to 18;

each $R_7$ is, independently, —OH, —$NH_2$, —O—Z, —N(Z)$_2$, —N($CH_2$—O—Z)$_2$, —N($CH_2$OH)$_2$, —N($CH_2CH_2$—O—Z)$_2$, —N($CH_2NH_2$)$_2$, —N($CH_2CH_2$OH)$_2$, —$CH_2$—O—Z, —$CH_2$—$NH_2$, —N($CH_3$)$_2$, —O-(alkylene)-$CH_3$, —$CH_2$—Y, —NCO, —O—C(=O)—($CH_2$)$_w$—$CH_3$, —NH—Z, —N[$CH_2$O—C(=O)—CH=$CH_2$]$_2$, —NH—C(=O)CH=$CH_2$, —$CH_2CH_2$—O—Z, —$CH_2CH_2$OH, —O—C(=O)—CH=$CH_2$, —N($CH_2$—$CH_2$—$NH_2$)$_2$, —($CH_2$—$CH_2$—O)$_w$H, —($CH_2$—$CH_2$—$CH_2$—O)$_w$H, —N[$CH_2$—$CH_2$—O—C(=O)—CH=$CH_2$]$_2$, or —N[$CH_2$—$CH_2$—NH—C(=O)—CH=$CH_2$]$_2$, where each w is, independently, an integer from 1 to 18;

$R_8$ is —OH, —$NH_2$, —O—Z, —N(Z)$_2$, —N($CH_2$—O—Z)$_2$, —N($CH_2$OH)$_2$, —N($CH_2CH_2$—O—Z)$_2$, —N($CH_2NH_2$)$_2$, —N($CH_2CH_2$OH)$_2$, —$CH_2$—O—Z, —$CH_2$—OH, —$CH_2$—$NH_2$, —N($CH_3$)$_2$, —O-(alkylene)-$CH_3$, —$CH_2$—Y, —NCO, —O—C(=O)—($CH_2$)$_x$—$CH_3$, —NH—Z, —N[$CH_2$O—C(=O)—CH=$CH_2$]$_2$, —NH—C(=O)CH=$CH_2$, —$CH_2CH_2$—O—Z, —$CH_2CH_2$OH, —O—C(=O)—CH=$CH_2$, —N($CH_2$—$CH_2$—$NH_2$)$_2$, —($CH_2$—$CH_2$—O)$_x$H, —($CH_2$—$CH_2$—$CH_2$—O)$_x$H, —N[$CH_2$—$CH_2$—O—C(=O)—CH=$CH_2$]$_2$, or —N[$CH_2$—$CH_2$—NH—C(=O)—CH=$CH_2$]$_2$, where each x is, independently an integer from 1 to 18;

Z is

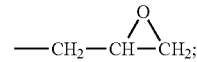

and

Y is Cl, Br, F, or I.

2. The compound of claim 1, wherein $R_1$, $R_2$, and $R_3$ are each independently H.

3. The compound of claim 1, wherein $R_4$ is —$NH_2$, —N($CH_3$)$_2$, —O—C(=O)—CH=$CH_2$, —NCO, —O—C(=O)—($CH_2$)$_r$—$CH_3$, —NH—C(=O)CH=$CH_2$, —O—Z, —O—($CH_2$)$_7$—$CH_3$, —NH—Z, or —N($CH_2CH_2$OH)$_2$.

4. The compound of claim 1, wherein $R_5$, $R_6$, $R_7$, and $R_8$ are each independently —$NH_2$, —N($CH_3$)$_2$, —O—C(=O)—CH=$CH_2$, —NCO, —O—C(=O)—($CH_2$)$_y$—$CH_3$, C(=O)CH=$CH_2$, —O—Z, —O—($CH_2$)$_7$—$CH_3$, —NH—Z, or —N($CH_2CH_2$OH)$_2$.

5. The compound of claim 1, wherein $R_1$ is —H, each $R_2$ is —H, $R_3$ is —H, $R_4$ is —NH—C(=O)CH=$CH_2$, $R_5$ is —NH—C(=O)CH=$CH_2$, $R_6$ is —NH—C(=O)CH=$CH_2$, each $R_7$ is —NH—C(=O)CH=$CH_2$, and $R_8$ is —NH—C(=O)CH=$CH_2$.

* * * * *

UNITED STATES PATENT AND TRADEMARK OFFICE
CERTIFICATE OF CORRECTION

PATENT NO. : 9,868,683 B2
APPLICATION NO. : 14/898420
DATED : January 16, 2018
INVENTOR(S) : Adam It is certified that error appears in the above-identified patent and that said Letters Patent is hereby corrected as shown below:

In the Specification

In Column 5, Line 25, delete "—$CH_2$—OH," and insert -- —$CH_2$—O—Z, —$CH_2$—OH, --, therefor.

In Column 5, Line 37, delete "—$CH_2$—OH," and insert -- —$CH_2$—O—Z, —$CH_2$—OH, --, therefor.

In Column 5, Line 50, delete "—$CH_2$—OH," and insert -- —$CH_2$—O—Z, —$CH_2$—OH, --, therefor.

In Column 5, Line 61, delete "—$CH_2$—OH," and insert -- —$CH_2$—O—Z, —$CH_2$—OH, --, therefor.

In Column 19, Line 31, delete "epichlorohyrin" and insert -- epichlorohydrin --, therefor.

In Column 21, Line 65, delete "examplary" and insert -- exemplary --, therefor.

In Column 22, Line 6, delete "analkanoyl" and insert -- an alkanoyl --, therefor.

In Column 22, Line 27, delete "examplary" and insert -- exemplary --, therefor.

In Column 22, Line 53, delete "examplary" and insert -- exemplary --, therefor.

In Column 23, Line 16, delete "examplary" and insert -- exemplary --, therefor.

In Column 26, Line 3, delete "aminogroups" and insert -- amino groups --, therefor.

In Column 31, Line 15, delete "recitation no" and insert -- recitation, no --, therefor.

In Column 31, Line 18, delete "one or more" and insert -- "one or more" --, therefor.

In Column 31, Line 25, delete "one or more or "at" least one" and insert -- "one or more" or "at least one" --, therefor.

Signed and Sealed this
Fifth Day of June, 2018

Andrei Iancu
*Director of the United States Patent and Trademark Office*

CERTIFICATE OF CORRECTION (continued)
U.S. Pat. No. 9,868,683 B2

In Column 31, Line 37, delete "general such" and insert -- general, such --, therefor.

In Column 31, Line 44, delete "general such" and insert -- general, such --, therefor.

In the Claims

In Column 34, Line 30, in Claim 4, delete "C(=O)CH=CH$_2$," and insert -- —NH—C(=O)CH=CH$_2$, --, therefor.